United States Patent
Lashure et al.

(10) Patent No.: US 12,383,324 B2
(45) Date of Patent: Aug. 12, 2025

(54) STRAIGHT AND CURVED FEMORAL BROACH IMPACTOR ADAPTERS

(71) Applicant: DEPUY SYNTHES PRODUCTS, INC., Raynham, MA (US)

(72) Inventors: Daniel E. Lashure, Fort Wayne, IN (US); Nathan C. Reeder, Warsaw, IN (US); Humberto Isaza, Warsaw, IN (US); Cory A. Shulaw, Warsaw, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 366 days.

(21) Appl. No.: 17/314,409

(22) Filed: May 7, 2021

(65) Prior Publication Data

US 2022/0354560 A1 Nov. 10, 2022

(51) Int. Cl.
| | |
|---|---|
| A61B 17/92 | (2006.01) |
| A61B 17/16 | (2006.01) |
| A61B 17/00 | (2006.01) |
| A61B 17/56 | (2006.01) |

(52) U.S. Cl.
CPC .......... *A61B 17/921* (2013.01); *A61B 17/164* (2013.01); *A61B 2017/00367* (2013.01); *A61B 2017/00486* (2013.01); *A61B 17/1668* (2013.01); *A61B 2017/564* (2013.01); *A61B 2017/925* (2013.01)

(58) Field of Classification Search
CPC . A61F 2/4607; A61B 17/1659; A61B 17/921; A61B 17/164
See application file for complete search history.

(56) References Cited

U.S. PATENT DOCUMENTS

| | | | |
|---|---|---|---|
| 6,663,636 B1 * | 12/2003 | Lin | A61B 17/1659 606/85 |
| 8,393,409 B2 | 3/2013 | Pedicini | |
| 8,602,124 B2 | 12/2013 | Pedicini | |
| 8,695,726 B2 | 4/2014 | Pedicini | |
| 8,936,105 B2 | 1/2015 | Pedicini | |
| 8,936,106 B2 | 1/2015 | Pedicini | |
| 9,901,354 B2 | 2/2018 | Pedicini | |
| RE46,954 E | 7/2018 | Pedicini | |
| RE46,979 E | 8/2018 | Pedicini | |
| 10,342,591 B2 | 7/2019 | Pedicini | |

(Continued)

FOREIGN PATENT DOCUMENTS

| | | |
|---|---|---|
| DE | 202006012836 U1 | 10/2006 |
| DE | 202008017199 U1 | 3/2009 |
| EP | 2777551 A1 * | 9/2014 ........... A61B 17/155 |

OTHER PUBLICATIONS

PCT International Search Report for International Application No. PCT/IB2022/053871, Jul. 22, 2022, 8 pages.

*Primary Examiner* — Sameh R Boles
(74) *Attorney, Agent, or Firm* — Barnes & Thornburg LLP

(57) ABSTRACT

An orthopaedic surgical instrument may include an elongated body with a broach end and an impactor end. The body may be straight or curved. A latch lever may be pivotally coupled to the elongated body. The latch lever may be moveable between an open position and a latched position in which the latch lever is retained within the body. A surgical broach may be rigidly attached to the broach end of the elongated body. An automated surgical impactor may be attached to the impactor end.

18 Claims, 20 Drawing Sheets

(56) References Cited

U.S. PATENT DOCUMENTS

| | | |
|---|---|---|
| 10,381,696 B2 | 8/2019 | Pedicini |
| 10,420,567 B2 | 9/2019 | Pedicini |
| 10,446,895 B2 | 10/2019 | Pedicini |
| 10,603,050 B2 | 3/2020 | Pedicini |
| RE47,963 E | 4/2020 | Pedicini |
| RE47,997 E | 5/2020 | Pedicini |
| RE48,184 E | 9/2020 | Pedicini |
| RE48,251 E | 10/2020 | Pedicini |
| RE48,387 E | 1/2021 | Pedicini |
| RE48,388 E | 1/2021 | Pedicini |
| 10,912,597 B2 | 2/2021 | Pedicini |
| 2014/0121650 A1 | 5/2014 | Thomsen et al. |
| 2014/0207200 A1* | 7/2014 | Kerboul ............ A61B 17/1659 606/86 R |
| 2018/0055552 A1 | 3/2018 | Pedicini |
| 2018/0055553 A1 | 3/2018 | Pedicini |
| 2018/0055554 A1 | 3/2018 | Pedicini |
| 2018/0338751 A1 | 11/2018 | Pedicini |
| 2019/0183554 A1 | 6/2019 | Pedicini |
| 2019/0223889 A1 | 7/2019 | Pedicini |
| 2019/0282286 A1 | 9/2019 | Pedicini |
| 2019/0305394 A1 | 10/2019 | Pedicini |
| 2020/0197028 A1 | 6/2020 | Pedicini |

* cited by examiner

STRAIGHT AND CURVED FEMORAL BROACH IMPACTOR ADAPTERS

TECHNICAL FIELD

The present disclosure relates generally to orthopaedic instruments for use in the performance of an orthopaedic joint replacement procedure, and more particularly to orthopaedic surgical instruments for use in the performance of a hip replacement procedure.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular prosthetic component and a femoral head prosthetic component. An acetabular prosthetic component generally includes an outer shell configured to engage the acetabulum of the patient and an inner bearing or liner coupled to the shell and configured to engage the femoral head. The femoral head prosthetic component and inner liner of the acetabular component form a ball and socket joint that approximates the natural hip joint.

Typical joint arthroplasty surgical procedures include impacting surgical instruments (e.g., broaches, chisels, or other cutting tools) and/or prosthetic implants into the patient's bone. Historically, impaction has been performed by an orthopaedic surgeon manually striking a surgical instrument using a surgical mallet or hammer. Such manual impaction can be unpredictable and imprecise. Additionally, typical manual impaction instruments may require the surgeon to hold the instrument with one hand and strike the instrument with a mallet held in the surgeon's other hand.

Certain automated surgical impactors are capable of performing a series of percussive impacts that each provide a controlled amount of impaction energy. An automated surgical impactor may be used with one or more adapters to connect to various surgical instruments and/or implants. Typical adaptors connect to the surgical instrument and/or implant using a rigid drive train including one or more drive shafts, gear trains, or other rigid mechanical connections.

SUMMARY

According to one aspect, an orthopaedic surgical instrument includes an elongated body, a first lever and a second lever, a leaf spring, and a pushbutton catch coupled to the elongated body. The elongated body extends from a first end to a second end. The first end is configured to be received by an automated surgical impactor. The first lever extends from a pivot end to a latch end. The pivot end is pivotally coupled to the elongated body. The second lever is pivotally coupled to the elongated body, and includes a hook extending toward a top surface of the elongated body. The leaf spring has a first end that is pivotally coupled to the first lever and a second end that is pivotally coupled to the second lever such that movement of the first lever causes movement of the second lever. The first lever is movable between a first position in which the latch end is spaced apart from the elongated body and a second position in which the latch end is captured by the pushbutton catch. When the first lever is in the second position the leaf spring urges the second lever to pivot the hook toward the top surface. In an embodiment, the elongated body comprises a curved segment between the pivot end of the first lever and the second end of the elongated body.

In an embodiment, the elongated body includes the top surface having an elongated opening defined therein, a bottom surface opposite the top surface and having an elongated opening defined therein, one or more inner walls extending between the elongated opening defined in the top surface and the elongated opening defined in the bottom surface, and a first cavity defined by the one or more inner walls. The second lever is positioned within the first cavity and the pivot end of the first lever is pivotally coupled to the elongated body within the first cavity. The latch end of the elongated lever extends out of the first cavity through the elongated opening defined in the top surface. The leaf spring is positioned within the first cavity.

In an embodiment, the elongated body includes a planar front surface positioned on the second end of the elongated body, and a circular aperture is defined in the planar front surface. The circular aperture opens into the first cavity. In an embodiment, the circular aperture defines a passageway into the internal cavity that is sized to receive a mounting post of the surgical broach. When the first lever is in the second position the hook of the second lever is positioned in the passageway. In an embodiment, a guide post extends outward from the planar front surface of the elongated body. The guide post is positioned between the circular aperture and the bottom surface.

In an embodiment, the orthopaedic surgical instrument further includes a stop pin coupled to the elongated body and positioned within the first cavity. When the first lever is in the first position a bottom surface of the pivot end of the first lever contacts the stop pin.

In an embodiment, the elongated body includes a first side wall and a second side wall opposite the first side wall, an opening defined in the first side wall, one or more inner walls extending inwardly from the opening in the first side wall, wherein the one or more inner walls define a second cavity, and a second opening defined in the top surface between the first end and the elongated opening, wherein the second opening opens into the second cavity. The pushbutton catch is positioned in the second cavity. When the first lever is in the second position, a latch extending downward from the latch ending is positioned in the second cavity and retained by the pushbutton catch. In an embodiment, the pushbutton catch is moveable between a first position in which the pushbutton catch engages the latch positioned within the second cavity and a second position in which the pushbutton catch does not engage the latch. In an embodiment, the orthopaedic surgical instrument further includes a second spring positioned in the second cavity. The second spring is configured to bias the pushbutton catch in the first position.

In an embodiment, the pushbutton catch includes a button surface positioned toward the first side wall of the elongated body, a pair of side walls extending from the button surface into the second cavity, a back wall that connects the pair of side walls, and a catch that extends from the back wall into the second cavity. In an embodiment, the latch of the elongated lever includes a first cam surface and the catch of the pushbutton catch includes a second cam surface. When the first lever is moved from the first position to the second position, the first cam surface engages the second cam surface, and when the first cam surface engages the second cam surface the pushbutton catch is urged from the first position to the second position.

According to another aspect, a method for performing an orthopaedic surgical procedure includes inserting a mounting post of a surgical broach into a circular aperture defined in a planar surface positioned at a first end of an orthopaedic surgical instrument; moving a first lever of the orthopaedic surgical instrument from a first position to a second position in response to inserting the mounting post into the circular aperture, wherein moving the first lever from the first position to the second position comprises latching the first lever in the second position, applying compression with a compliant member of the orthopaedic surgical instrument on a second lever of the orthopaedic surgical instrument, and clamping a hook of the second lever against the mounting post of the surgical broach; and coupling a second end of the orthopaedic surgical instrument to an automated surgical impactor in response to moving the lever.

In an embodiment, clamping the hook of the second lever against the mounting post comprises engaging a notch defined in the mounting post with a first side of a curved outer surface of the hook. In an embodiment, inserting the mounting post comprises engaging a second side of the curved outer surface of the hook with a chamfer defined in a tip of the mounting post, wherein engaging the second side comprises pivoting the hook away from a centerline of the circular aperture.

In an embodiment, the method further comprises impacting the surgical broach with the automated surgical impactor into a surgically prepared bone of a patient in response to coupling the second end to the automated surgical impactor; depressing a pushbutton catch of the orthopaedic surgical instrument in response to impacting the broach, wherein depressing the pushbutton catch comprises unlatching the second lever from the second position and releasing compression with the compliant member; and releasing the surgical broach from the first end of the orthopaedic surgical instrument in response to depressing the pushbutton catch.

In an embodiment, the method further comprises extracting the surgical broach with the automated surgical impactor from the surgically prepared bone in response to impacting the surgical broach; wherein depressing the pushbutton catch comprises depressing the pushbutton catch in response to extracting the surgical broach. In an embodiment, the method further comprises inserting a mounting post of second surgical broach into the circular aperture defined in the planar surface positioned at the first end of the orthopaedic surgical instrument in response to releasing the surgical broach.

According to another aspect, a surgical instrument assembly includes an orthopaedic surgical instrument and a surgical broach. The orthopaedic surgical instrument includes an elongated body, a first lever and a second lever, a leaf spring, and a pushbutton catch coupled to the elongated body. The elongated body extends from a first end to a second end. The first end is configured to be received by an automated surgical impactor. T first lever extends from a pivot end to a latch end. The pivot end is pivotally coupled to the elongated body, and the second lever is also pivotally coupled to the elongated body. The second lever includes a hook extending toward a top surface of the elongated body. The leaf spring has a first end that is pivotally coupled to the first lever and a second end that is pivotally coupled to the second lever such that movement of the first lever causes movement of the second lever. The surgical broach includes a mounting post extending from a first end of the surgical broach, and the surgical broach is coupled to the second end of the orthopaedic surgical instrument. The first lever of the orthopaedic surgical instrument is movable between a first position in which the latch end is spaced apart from the elongated body and a second position in which the latch end is captured by the pushbutton catch. When the first lever is in the second position the leaf spring urges the second lever to pivot the hook into engagement with the mounting post of the surgical broach.

In an embodiment, the elongated body includes the top surface having an elongated opening defined therein, a bottom surface opposite the top surface and having an elongated opening defined therein, one or more inner walls extending between the elongated opening defined in the top surface and the elongated opening defined in the bottom surface, and a first cavity defined by the one or more inner walls. The second lever is positioned within the first cavity. The pivot end of the first lever is pivotally coupled to the elongated body within the first cavity. The latch end of the elongated lever extends out of the first cavity through the elongated opening defined in the top surface. The leaf spring is positioned within the first cavity.

BRIEF DESCRIPTION OF THE DRAWINGS

The detailed description particularly refers to the following figures, in which.

DETAILED DESCRIPTION OF THE DRAWINGS

Figure 1:
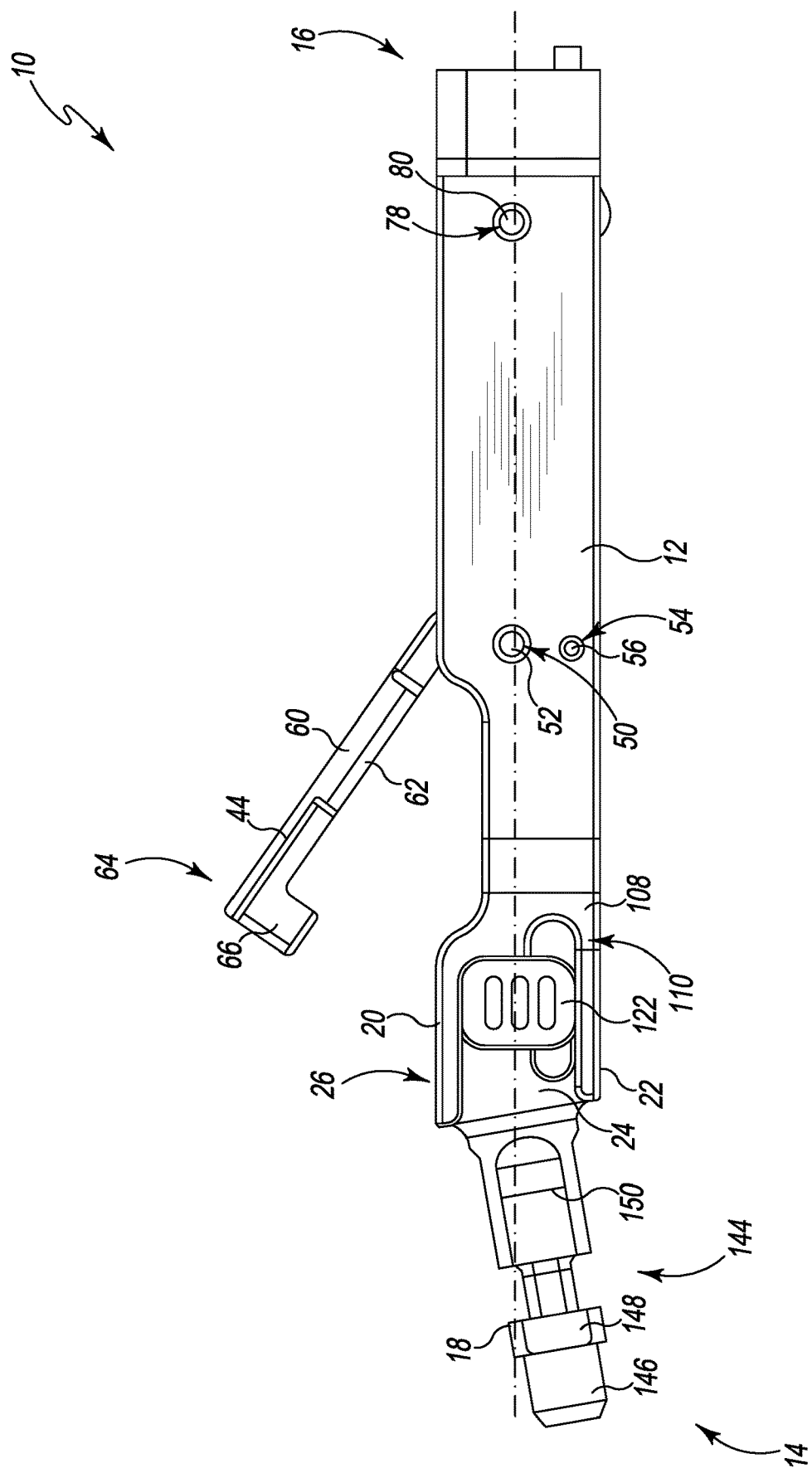
FIG. 1 is a perspective view of straight broach impactor adapter in an open configuration.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise. Additionally, it is to be understood that terms such as top, bottom, front, rear, side, height, length, width, upper, lower, and the like that may be used herein merely describe points of reference and do not necessarily limit embodiments of the present disclosure to any particular orientation or configuration.

Referring now to FIGS. 1-5, a straight femoral broach impactor adapter 10 (hereinafter impactor adapter 10) is shown. The impactor adapter 10 is an orthopaedic surgical instrument; that is, a surgical tool used by a surgeon in performing an orthopaedic surgical procedure. As such, it should be appreciated that, as used herein, the terms "orthopaedic surgical instrument" and "orthopaedic surgical instruments" are distinct from orthopaedic implants or prostheses that are surgically implanted in the body of the patient. As described further below, the impactor adapter 10 may be used with an automated surgical impactor to drive a femoral broach into a patient's surgically prepared femur.

As shown in FIGS. 1-4, the impactor adapter 10 includes an elongated body 12 extending from an angled impactor attachment end 14 to a broach end 16. In the illustrative embodiment, the body 12 is formed from metallic material, such as, for example, stainless steel or cobalt chromium. The body 12 is generally linear and defines a longitudinal tool axis 18. As described further below, in use the impactor end 14, also called the rear end or the proximal end, may be attached to an automated surgical impactor tool. Similarly, in use the broach end 16, also called the tip end, the front end, or the distal end, may be attached to a surgical broach, chisel, or other surgical cutting tool.

The elongated body 12 is generally rectangular in cross section and thus has a top surface 20 and a bottom surface 22 opposite the top surface 20, as well as a pair of side surfaces 24, 26. A pair of elongated openings 28, 30 are defined in each of the top surface 20 and the bottom surface 22, respectively. One or more inner walls 32 extend between the openings 28, 30 through the body 12 and define a cavity 34 inside the body 12.

The broach end 16 includes a planar surface 36 having a circular aperture 38 defined thereon. A passageway 40 extends inward from the circular aperture 38 into the cavity 34. A guide pin 42 positioned on the planar surface 36 between the circular aperture 38 and the bottom surface 32 extends outward from the planar surface 36. As described further below, when the impactor adaptor 10 is coupled to a femoral surgical broach, the aperture 38 receives a mounting post of the broach.

The impactor adapter 10 further includes an elongated latch lever 44 that extends outward from the cavity 34 through the opening 28 defined in the top surface 20. The latch lever 44 includes a pivot end 46 that is pivotally mounted to the body 12 within the cavity 34. Illustratively, a bore 48 is defined through the pivot end 46, and a pair of circular openings 50 are defined through the side surfaces 24, 26 of the body 12. The bore 48 encompasses the pivot point of the latch lever 44. A pin 52 is positioned in the bore 48 and the openings 50 such that the latch lever 44 is joined with the body 12 and is allowed to rotate about the pin 52. In the illustrative embodiment, the pin 52 is press-fit into the openings 50; however, any suitable method of securing the pin 52 may be used.

Figure 2:
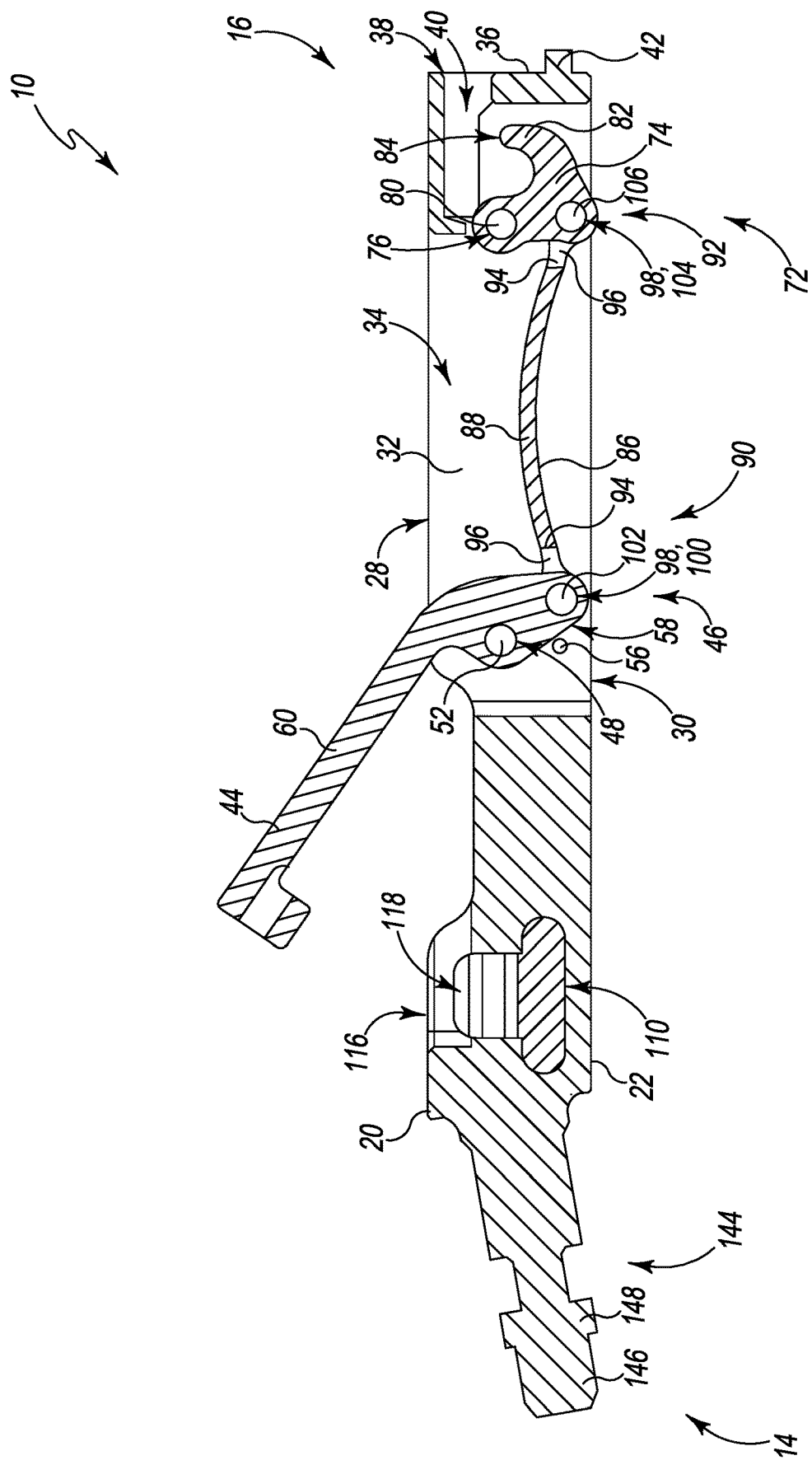
FIG. 2 is a cross-sectional elevation view of the straight broach impactor adapter of FIG. 1.

Another pair of circular openings 54 is defined through the side surfaces 24, 26 of the body 12. A stop pin 56 is positioned in the openings 54. In the illustrative embodiment, the stop pin 56 is press-fit into the openings 54; however, any suitable method of securing the stop pin 56 may be used. As shown in FIG. 2, as the lever 44 reaches an open position, a lower surface 58 of the pivot end 46 engages the stop pin 56. Thus, the stop pin 56 operates as a stop that limits range of motion for the lever 44.

Figure 3:
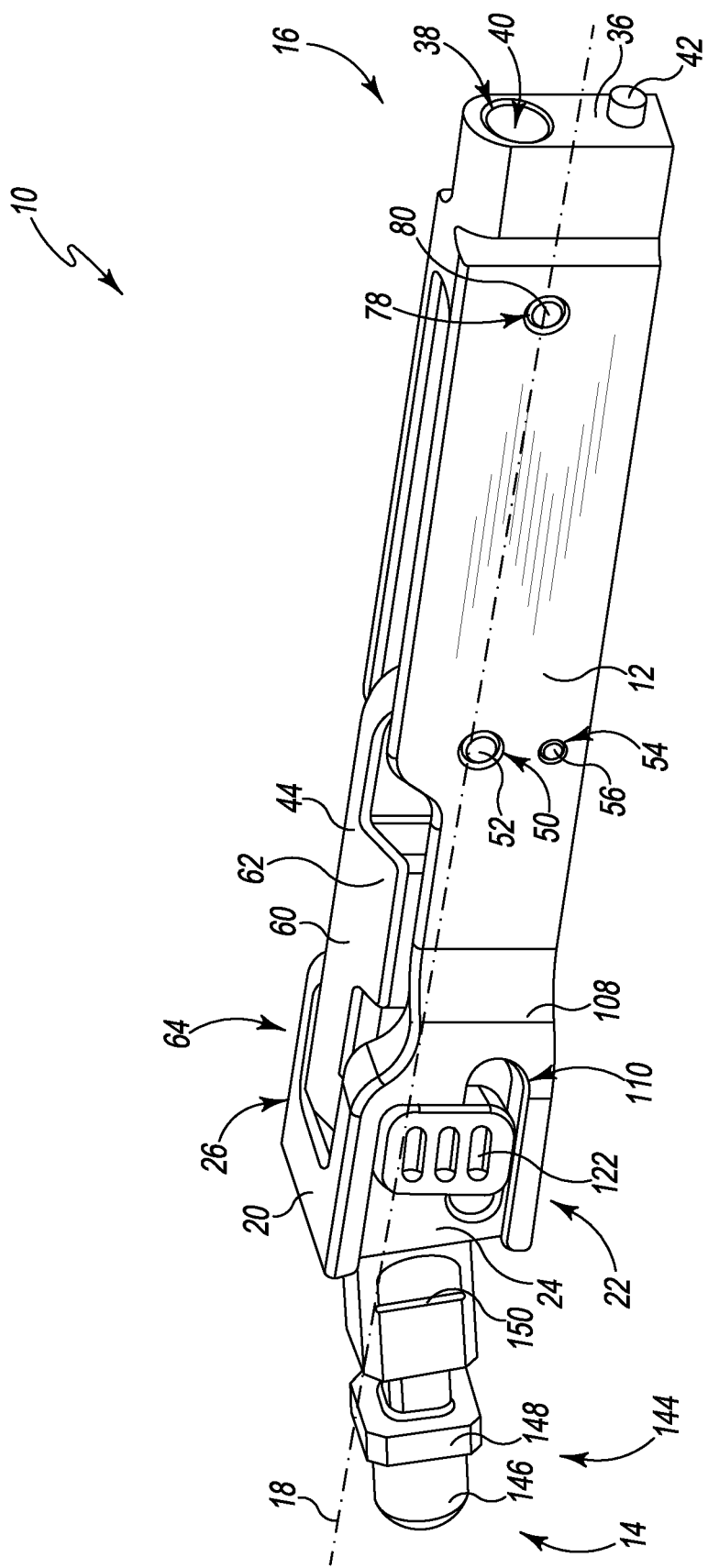
FIG. 3 is a perspective view of the straight broach impactor adapter of FIG. 1 in a latched configuration.
Figure 4:
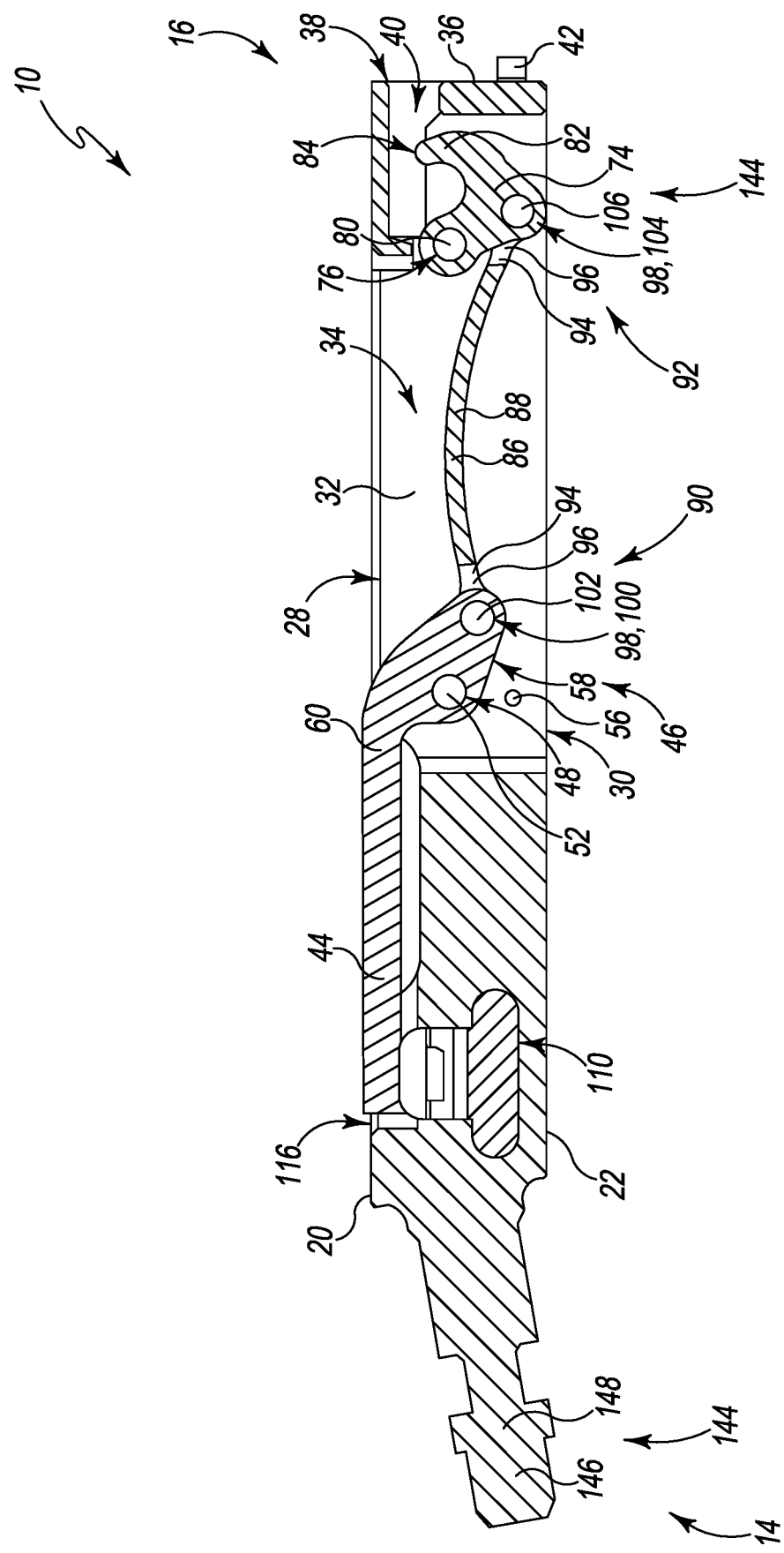
FIG. 4 is a cross-sectional elevation view of the straight broach impactor adapter of FIG. 3.
Figure 5:
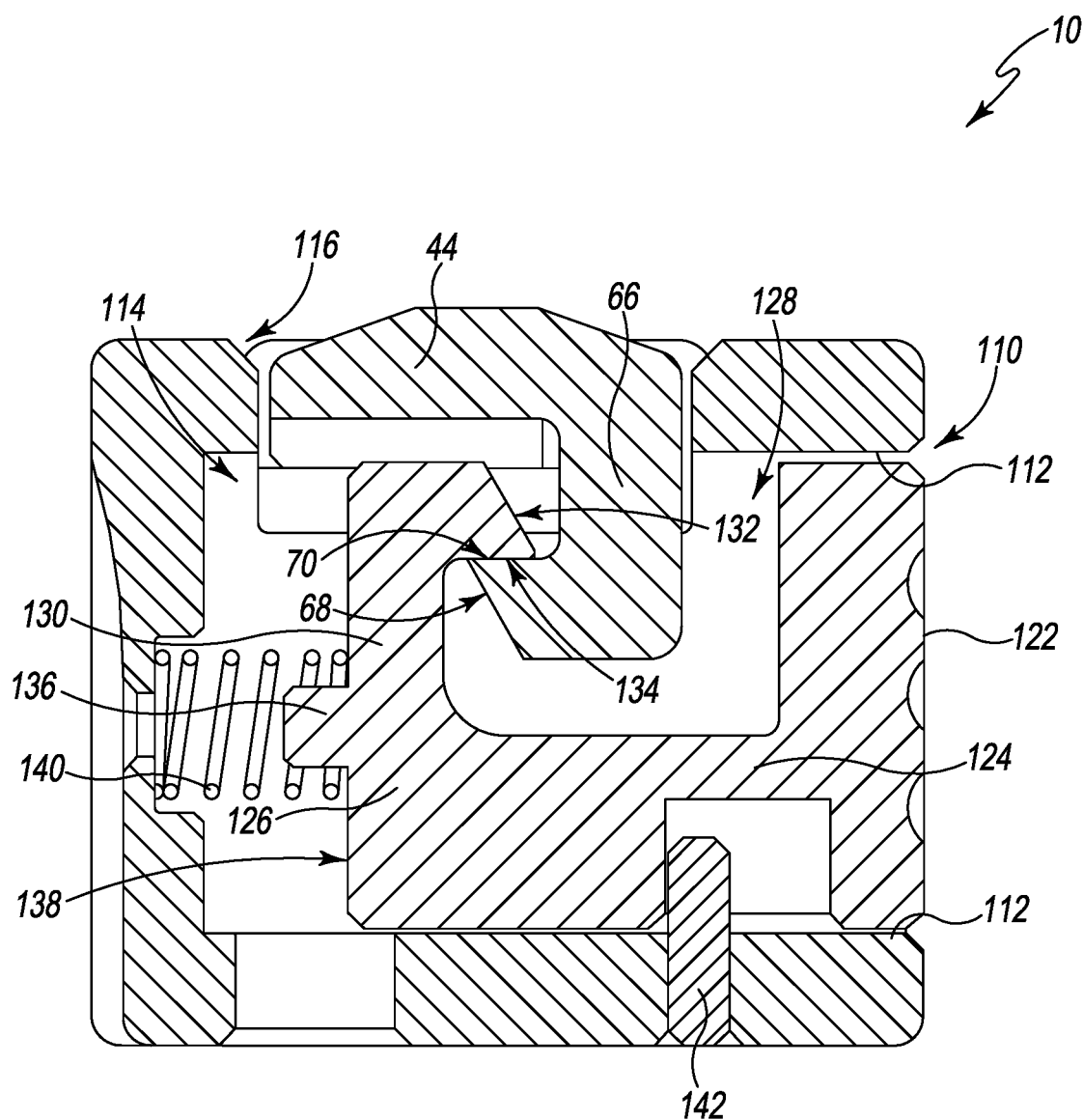
FIG. 5 is a cross-sectional rear elevation view of the straight broach adapter of FIG. 3.

A body 60 of the latch lever 44 extends from the pivot end 46 outward from the opening 28 defined in the top surface 20. A wing 62 extends laterally from the body 60. The body 60 extends further toward a latch end 64. The latch end 64 includes a latch 66 extending downward from the lever body 60. As shown in the cross-sectional view of FIG. 5, the latch 66 includes a lower cam surface 68 and an upper surface 70 that extend inward toward the interior of the body 12. As described further below, when the lever 44 is in a latched position as shown in FIGS. 3-5, the latch 66 of the latch lever 44 may be captured within the body 12 by a catch mechanism.

In the latched position, the body 60 of the lever 44 may contact the top surface 20 of the body 12, operating as a stop that limits range of motion of the lever 44. In the latched position, the wing 62 of the lever 44 extends outward past the side surface 24, allowing the surgeon or other user to grip the lever 44. As described above, the latch lever 44 is moveable between the open position shown in FIGS. 1-2 and the latched position shown in FIGS. 3-5. The throw of the lever 44, that is, the angle between the body 60 of the lever 44 and the body 12 when the lever 44 is in the fully open position may be limited to less than about 40-45 degrees.

The impactor adapter 10 further includes a clamp lever 72 positioned within the cavity 34. The clamp lever 72 includes a body 74 having a roughly triangular, non-linear shape. The clamp lever 72 is pivotally mounted to the body 12 within the cavity 34. Illustratively, a bore 76 is defined through lever body 74, and a pair of circular openings 78 are defined through the side surfaces 24, 26 of the body 12. The bore 76 encompasses the pivot point of the clamp lever 72. A pin 80 is positioned in the bore 76 and the openings 78 such that the clamp lever 72 is joined with the body 12 and is allowed to rotate about the pin 80. In the illustrative embodiment, the pin 80 is press-fit into the openings 78; however, any suitable method of securing the pin 80 may be used.

The clamp lever 72 extends to a bullnose hook 82 having a convex, rounded outer surface 84. As the clamp lever 72 rotates about the pin 80, the hook 82 pivots toward and away from the top surface 20 within the cavity 34. As described further below, the hook 82 of the clamp lever 72 is operable to securely attach a surgical broach to the impactor adapter 10.

The impactor adapter 10 further includes a leaf spring 86 or other compliant connecting member that connects the latch lever 44 and the clamp lever 72. The leaf spring 86 includes a flexible body 88 that extends between ends 90, 92. The end 90 is pivotally coupled to pivot end 46 of the latch lever 44, and the end 92 is pivotally coupled to the body 74 of the clamp lever 72. Illustratively, each end 90, 92 includes a fork 94 that extends to a pair of mounting plates 96. A circular opening 98 is defined through each mounting plate 96. The mounting plates 96 of the end 90 surround a bore 100 defined through the pivot end 46 of the lever 44. A pin 102 is positioned in the openings 98 and the bore 100 to pivotally couple the end 90 to the lever 44. Similarly, the mounting plates 96 of the end 92 surround a bore 104 defined through the clamp lever 72, and a pin 106 is positioned in the openings 98 and the bore 104 to pivotally couple the end 92 to the clamp lever 72.

When the lever 44 is in the open position (shown in FIGS. 1-2), the leaf spring 86 has a relaxed, arcuate shape. When the lever 44 is moved to the latched position (shown in FIGS. 3-5), the leaf spring 86 has a relatively shortened and compressed shape, causing the leaf spring 86 to be in compression. When in compression, the leaf spring 86 urges the clamp lever 72 to pivot about the pin 80, rotating the hook 82 toward the top surface 20 of the body 12. Compression on the leaf spring 86 may be released by moving the lever 44 from the latched position to the open position as described further below. As described above, the wing 62 extending from the lever body 60 may assist the surgeon or other user in moving the lever 44 from the latched position to the open position.

As shown in FIGS. 1 and 3, each of the side surfaces 24, 26 has a waist 108 positioned between the cavity 34 and the impactor end 14. At the waist 108, the distance between the side surfaces 24, 26 increases toward the impactor end 14. As shown in FIG. 3, in the closed position, the wing 62 is positioned between the waist 108 and the broach end 14 and extends past the side surface 24, allowing the surgeon to grip the wing 62.

As shown in FIGS. 1-5, an opening 110 is defined in the side surface 24 of the body 12 between the waist 108 and the impactor end 14 of the body 12. One or more inner walls 112 extend inwardly from the opening 110, defining a cavity 114. An additional opening 116 is defined in the top surface 20. A passageway 118 extends through the opening 116 into the cavity 114.

A pushbutton catch 120, also referred to as a button 120, is positioned within the cavity 114. As described further below, the pushbutton catch 120 may be used to selectively retain the latch lever 44 in the latched position shown in FIGS. 3-5. The pushbutton catch 120 includes a button surface 122 positioned toward the side surface 24 of the body 12. The button surface 122 is configured to be pressed by a surgeon and thus may be textured or otherwise configured to provide additional grip. Additionally, as shown in FIG. 5, in ordinary operation the button surface 122 may be flush with the side surface 24 and/or recessed within the cavity 114 in order to prevent accidental operation.

The pushbutton catch 120 further includes a pair of side walls 124 that extend inward from the button surface 122 into the cavity 114. The side walls are connected by a back wall 126. Together, the button surface 122, the side walls 124, and the back wall 126 surround a button cavity 128. A catch 130 extends upward from the back wall 126. The catch 130 includes an upper cam surface 132 and a lower surface 134 that extend inward into the button cavity 128. A guide pin 136 extends from a back surface 138 of the catch 130 toward the other side surface 26. A helical spring 140 is retained between the body 12 and the back surface 138 of the catch 130, and the guide pin 136 is captured within the spring 140. The spring 140 urges against the body 12 and the back surface 138 to bias the pushbutton catch 120 toward the opening 110 in the side surface 24. A stop pin 142 positioned in a hole defined through the bottom surface 22 of the body 12 extends into the latch cavity 114. When the pushbutton catch 120 is positioned in the cavity 114, the stop pin 142 also extends into the button cavity 128. The stop pin 142 engages the back wall 126 of the pushbutton catch 120 and thus retains the pushbutton catch 120 within the cavity 114 of the body 12.

As shown in FIG. 5, when the lever 44 is in the latched position, the latch 66 extends into the cavity 114 and into the button cavity 128. The upper surface 70 of the latch 66 engages the lower surface 134 of the catch 130, thereby retaining the latch 66 within the button cavity 128. When the surgeon or other user depresses the button surface 162, the pushbutton catch 120 slides toward the side surface 26, and the lower surface 134 of the catch 130 slides off the upper surface 70, releasing the latch 66. When the latch 66 is released, the leaf spring 86 causes the latch end 64 of the lever 44 to swing out of the cavity 114 toward the open position, which releases compression of the leaf spring 86.

When a surgeon or other user moves the lever 44 from the open position to the latched position without depressing the pushbutton catch 120, the lower cam surface 68 of the latch 66 engages the upper cam surface 132 of the catch 130. This engagement of the cam surfaces 68, 132 forces the pushbutton catch 120 to slide toward the side surface 26, allowing the latch 66 to enter the button cavity 128. When the latch 66 passes the catch 120 and the cam surfaces 68, 132 disengage, the spring 140 forces the pushbutton catch 120 to slide back toward the side surface 24, which causes the lower surface 134 of the catch 130 to retain the upper surface 70 of the latch 66. Accordingly, the latch lever 44 may be operated with a single hand.

As shown in FIGS. 1-4, the impactor end 14 includes a shank 144, which is configured to be received by an automated surgical impactor. As shown in FIGS. 1 and 3, the shank 144 extends at a nonzero angle away from the tool axis 18. This nonzero angle may improve ergonomics for the surgeon when used with an automated surgical impactor. The illustrative shank 144 includes a pin 146 and a flange 148. The shank 144 is configured to be impacted by the automated surgical impactor in either a forward direction (i.e., to advance the impactor adaptor 10 toward the patient's bone) or a reverse direction (i.e., to back the impactor adaptor 10 out of the patient's bone). In other embodiments, it should be understood that the shank 144 may include any other configuration of pins, flanges, flats, and/or other features configured to captured and/or impacted by the automated surgical impactor. The illustrative shank 144 further includes a groove 150, which marks a depth at which the shank 144 is fully seated within the automated surgical impactor.

The impactor adapter 10 may be utilized during the performance of an orthopaedic surgical procedure similar to that shown in FIGS. 6-10. Initially, the surgeon surgically prepares the patient's bone to receive a surgical broach. To do so, the surgeon or other member of the surgical team may resect the patient's femur to remove the natural femoral head and create a substantially planar proximal surface on the patient's femur. The surgeon may use an osteotome to create an opening into the femoral canal.

Figure 6:
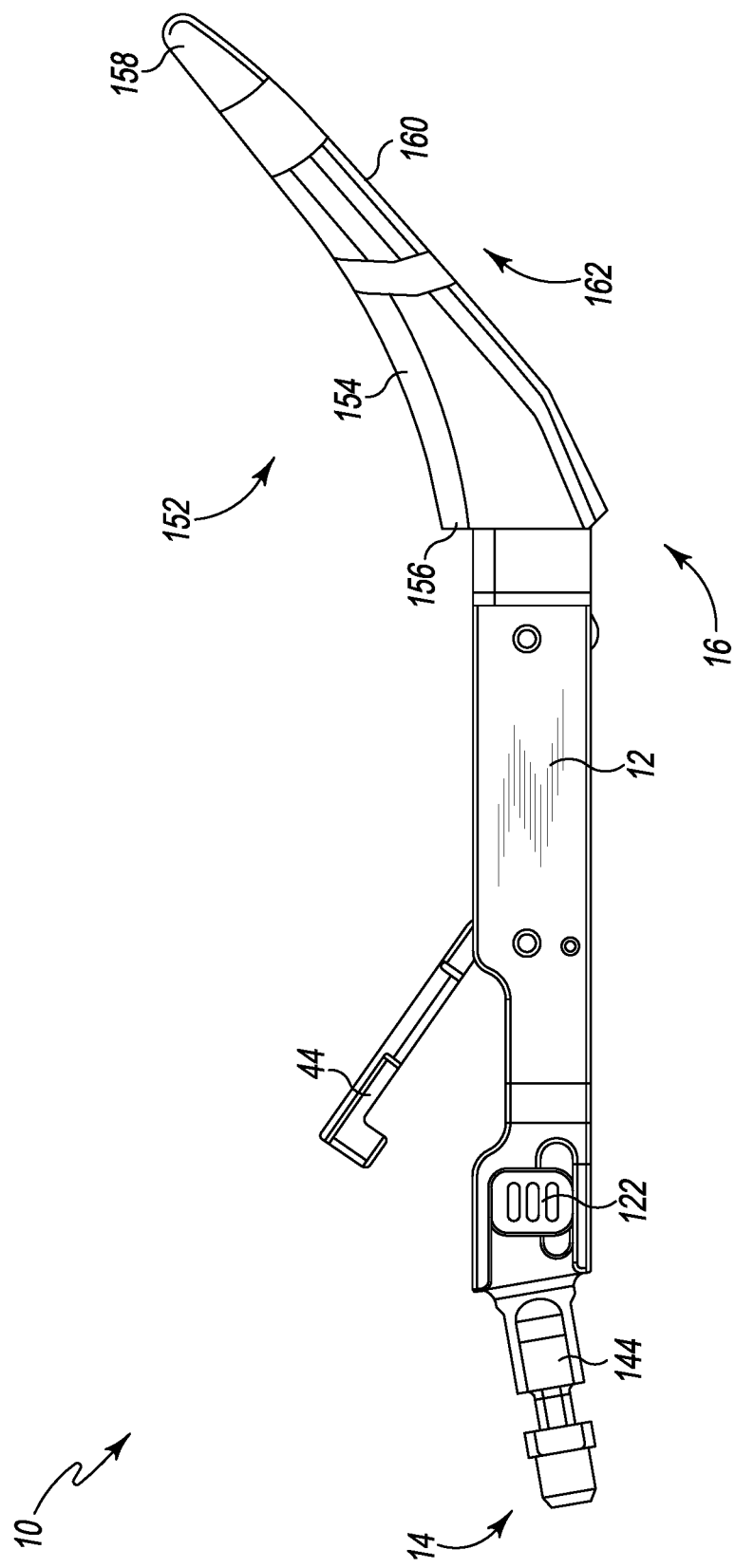
FIG. 6 is an elevation view of the straight broach impactor adapter of FIGS. 1-5 coupled to a femoral broach and in the open configuration.
Figure 7:
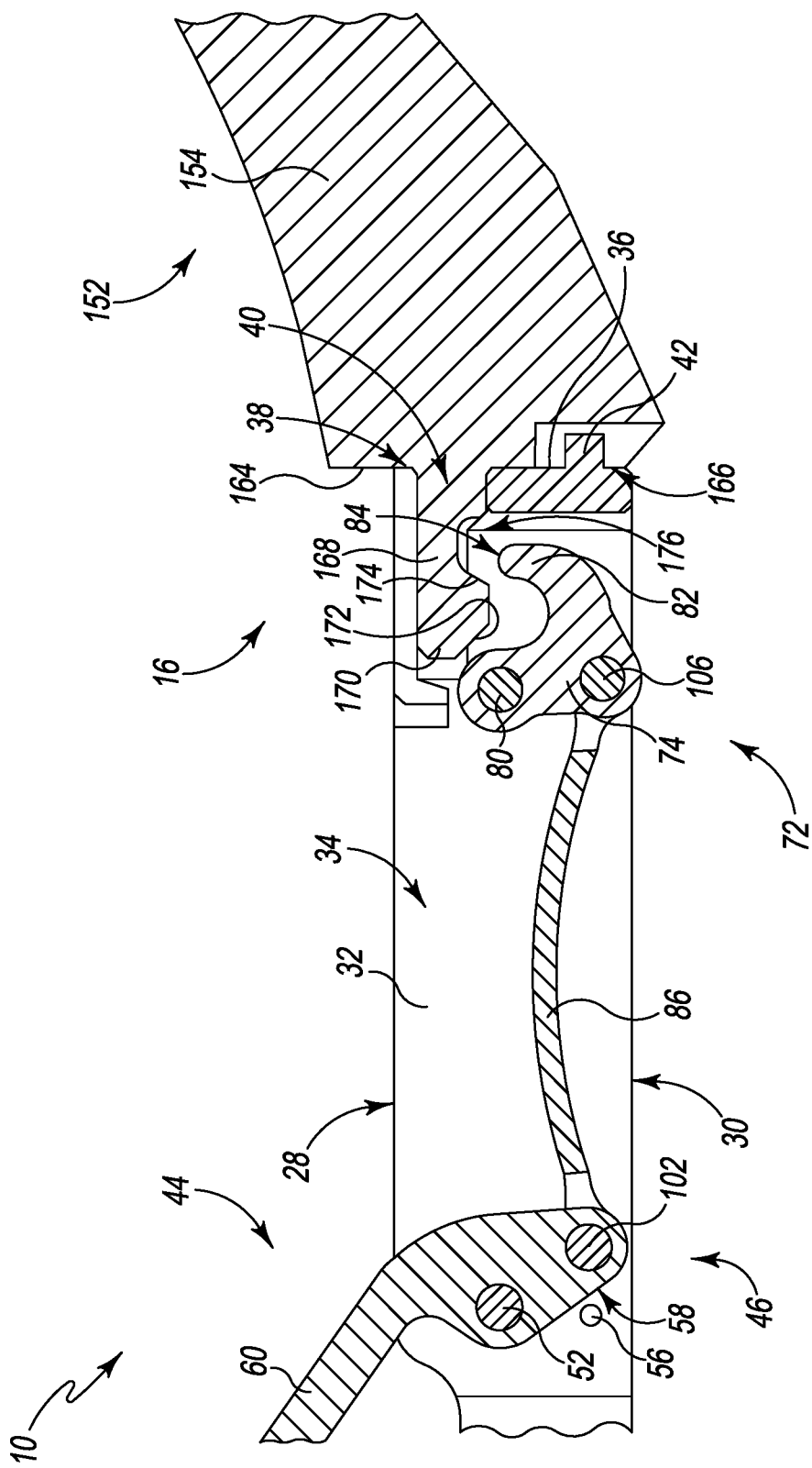
FIG. 7 is a fragmentary cross-sectional elevation view of the straight broach impactor adapter and the femoral broach of FIG. 6.

After preparing the patient's bone, and as shown in FIGS. 6-7, the surgeon attaches a femoral broach 152 to the impactor adapter 10. The surgeon may select the broach 152 from a collection of broaches 152 that each have a different size. As described further below, the surgeon may sequentially broach the patient's femur with a series of broaches 152 of increasing size.

The illustrative femoral broach 152 includes an elongated body 154 that extends from a proximal end 156 to a distal tip 158. In the illustrative embodiment, the femoral broach 152 is formed as a single monolithic component from a metallic material such as stainless steel. A tapered outer surface 160 extends from the proximal end 156 to the distal tip 158, and in some embodiments is covered with a plurality of cutting teeth 162. Each tooth 162 may be shaped and sized to surgically prepare the femoral canal of the patient's femur to receive a femoral component and/or another surgical instrument (e.g., another femoral broach and/or a femoral trial component).

The femoral broach 152 includes a planar proximal surface 164 at the proximal end 156 of the elongated body 154. As shown in FIG. 7, a slot 166 is defined in the proximal surface 164, which is sized to receive the guide pin 42 that extends from the broach end 16 of the impactor adapter 10. The broach 152 further includes a proximal mounting post 168 that extends outward from the surface 164 to a tip 170. The post 168 further defines a chamfer 172 positioned on the tip 170. An inner wall 174 defines a notch 176, which may be used to secure the femoral broach 152 to the impactor adaptor 10 as discussed further below.

As shown in FIG. 6, the lever 44 of the impactor adapter 10 is initially in the open position. The surgeon or other user attaches the proximal end 156 of the femoral broach 152 to the broach end 16 of the impactor adapter 10. As shown in FIG. 7, as the broach 152 and the impactor adaptor 10 are attached, the mounting post 168 of broach 152 passes through the aperture 38 of the impactor adapter 10 into the passageway 40, and the guide pin 42 of the impactor adapter 10 passes through the slot 166 of the broach 152. As the mounting post 168 enters the passageway 40, depending on the position of the clamp lever 72, the mounting post 168 may contact the bullnose hook 82 of the clamp lever 72. If so, the chamfer 172 on the tip 170 of mounting post 168 engages the convex outer surface 84 of the hook 82. As the chamfer 172 and the outer surface 84 are in engagement, the hook 82 is urged to rotate downward away from the passageway 40, allowing the mounting post 168 to continue entering the passageway. When the broach 152 is fully inserted into the impactor adaptor 10, the proximal surface 164 of the broach 152 contacts the planar surface 36 of the impactor adaptor. When fully inserted, the notch 176 defined in the mounting post 168 faces the bullnose hook 82 of the clamp lever 72.

Figure 8:
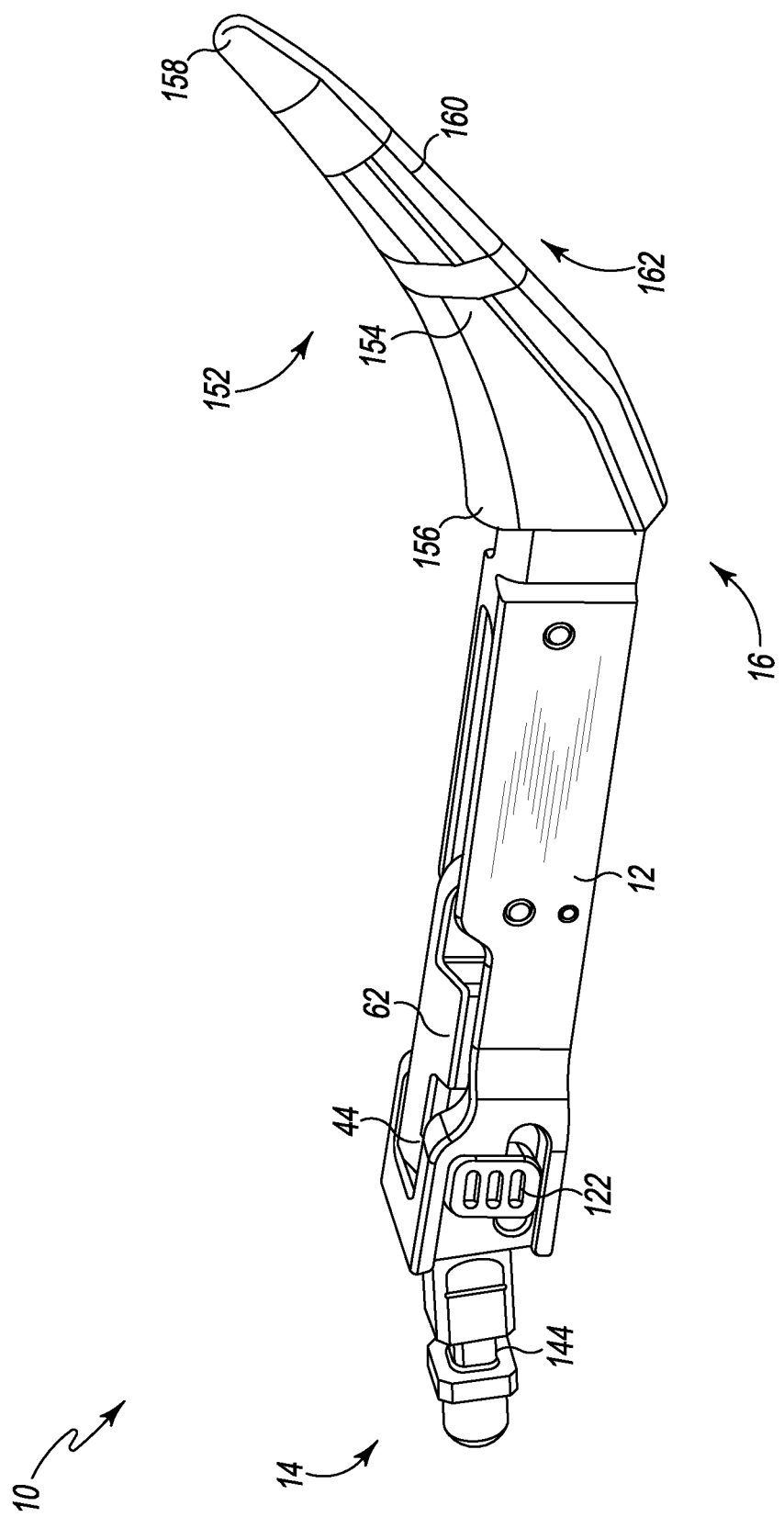
FIG. 8 is an elevation view of the straight broach impactor adapter of FIGS. 1-5 attached to the femoral broach and in the latched configuration.
Figure 9:
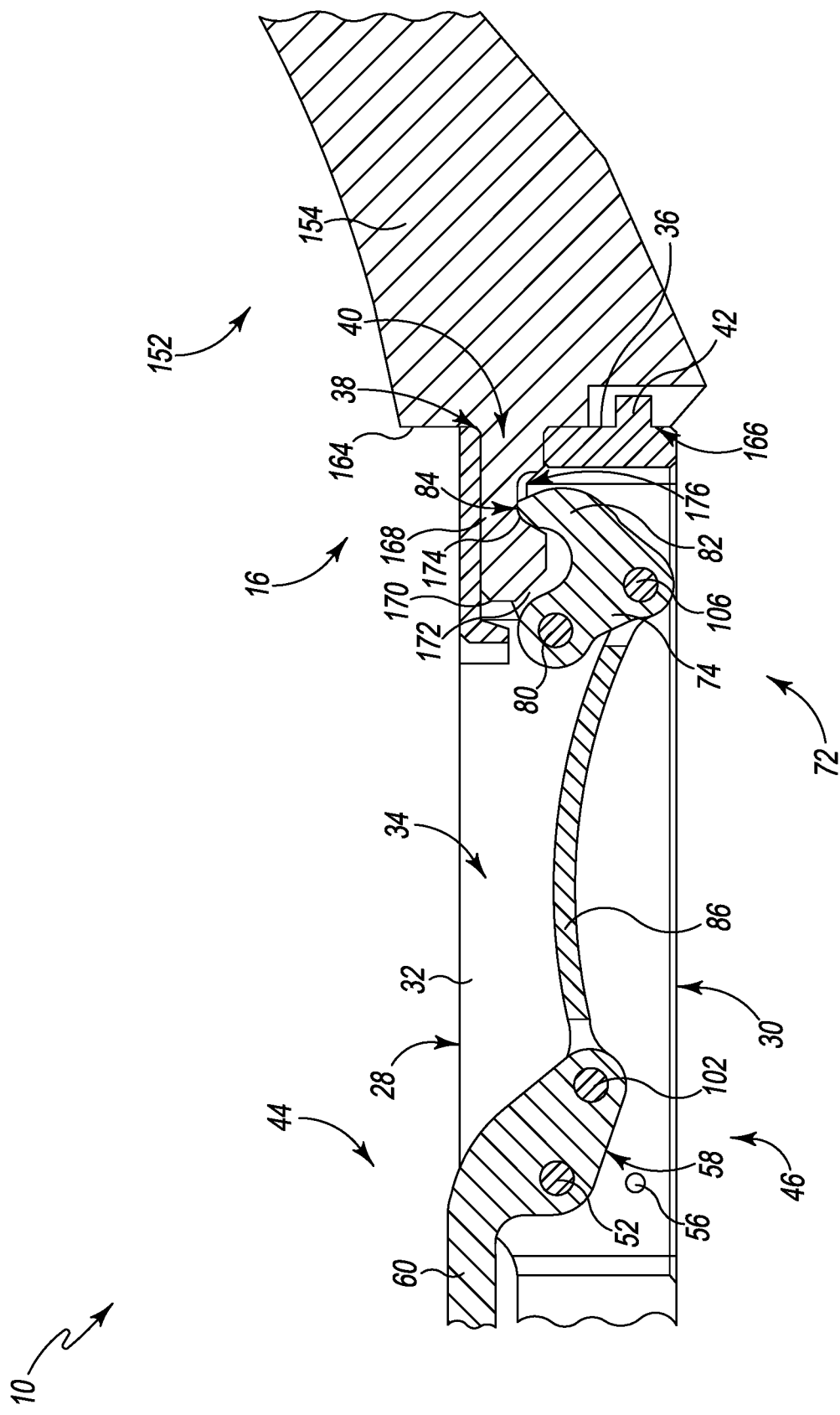
FIG. 9 is a fragmentary cross-sectional elevation view of the straight broach impactor and the femoral broach of FIG. 8.

After securing the femoral broach 152 to the impactor adaptor 10, the surgeon moves the latch lever 44 from the open position to the latched position, as shown in FIGS. 8-9. As the latch lever 44 is moved to the latched position, the leaf spring 86 is compressed. As the leaf spring 86 is placed in compression, the leaf spring 86 exerts a force on the clamp lever 72, causing the hook 82 of the clamp lever 72 to pivot toward the mounting post 168. The clamp lever 72 pivots until the outer surface 84 of the hook 82 engages the inner wall 174 within the notch 176. When in engagement, the leaf spring 86 and the clamp lever 72 exert a clamping force on the mounting post 168 that retains the femoral broach 152 against the surface 36 of the impactor adapter 10. The femoral broach 152 is thus held rigid and immobile against the implant adapter 10. As described above, when the latch lever 44 is in the latched position, the pushbutton catch 120 retains the latch 66, ensuring that the latch lever 44 remains in the latched position and that the femoral broach 152 remains rigidly attached to the impactor adaptor 10. Additionally, as the latch lever 44 is retained by the pushbutton catch 120, the leaf spring 86 is not extended to an over-center position in order to retain the latch lever 44. Thus, the impactor adapter 10 may have reduced wear and increased longevity as compared to impaction tools that use an over-center clamp function.

Figure 10:
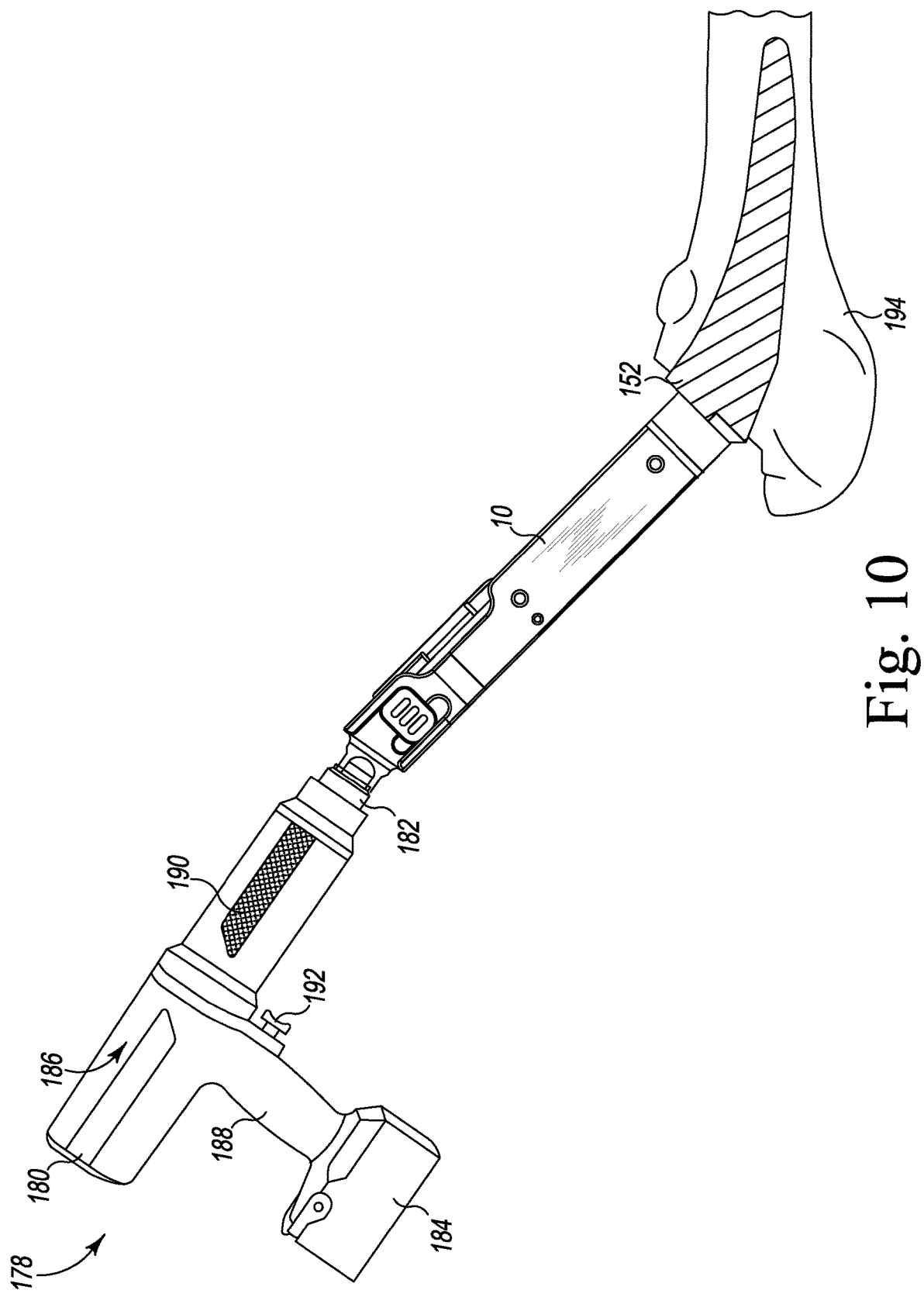
FIG. 10 is a perspective view of the straight broach impactor adapter and the femoral broach of FIGS. 8-9 during the performance of an orthopaedic surgical procedure using an automated surgical impactor.
Figure 11:
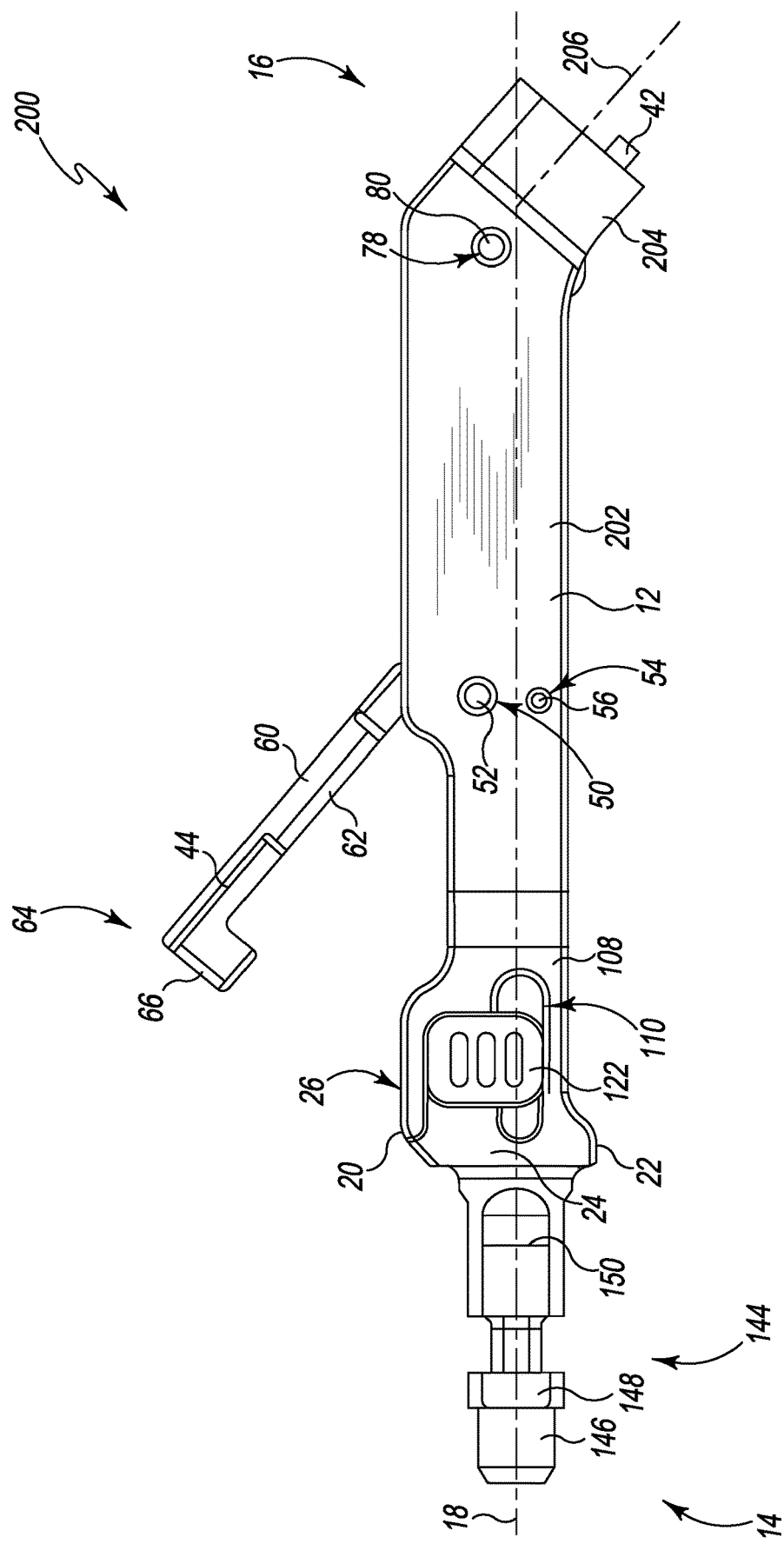
FIG. 11 is a perspective view of curved broach impactor adapter in an open configuration.
Figure 12:
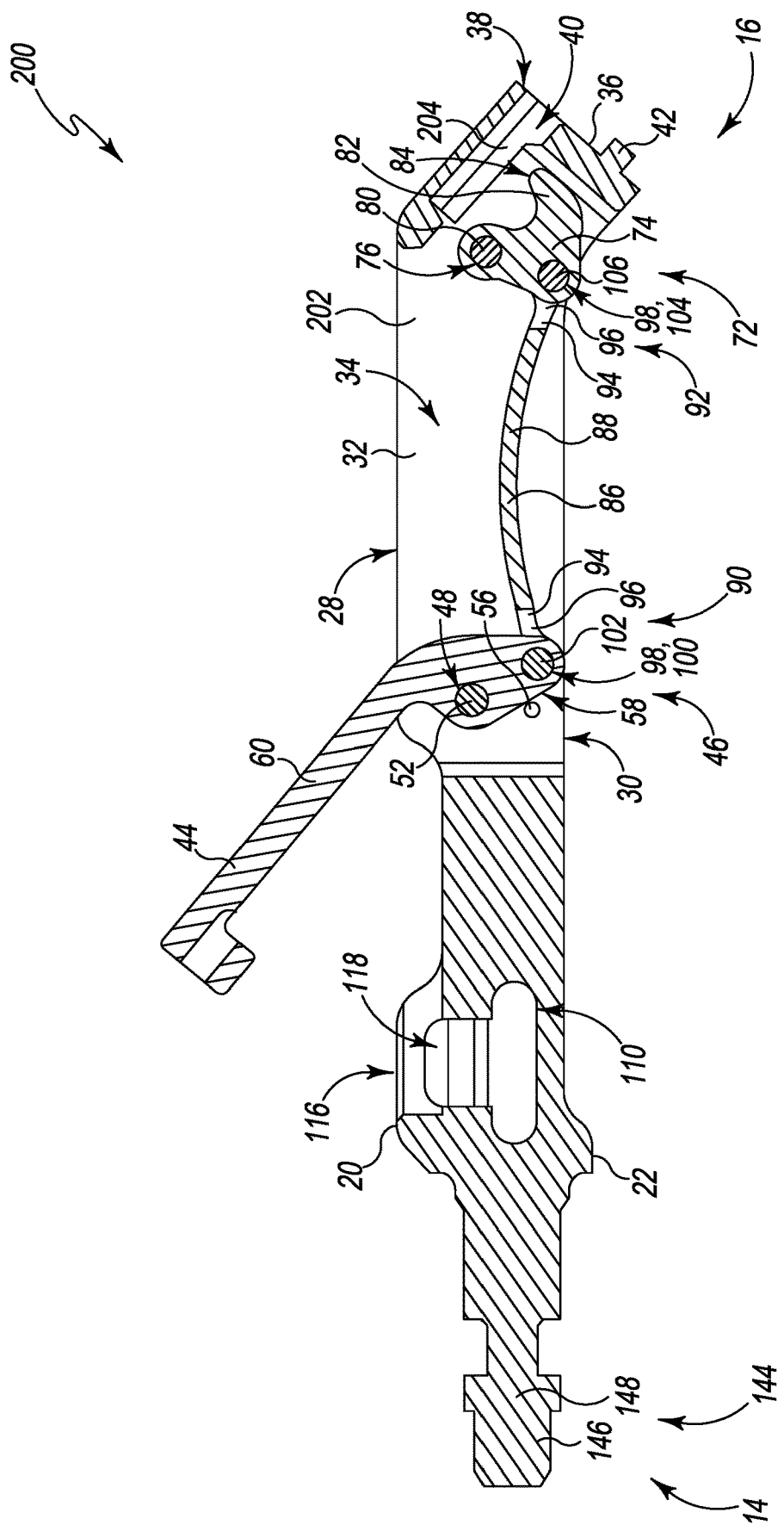
FIG. 12 is a cross-sectional elevation view of the curved broach impactor adapter of FIG. 11.
Figure 13:
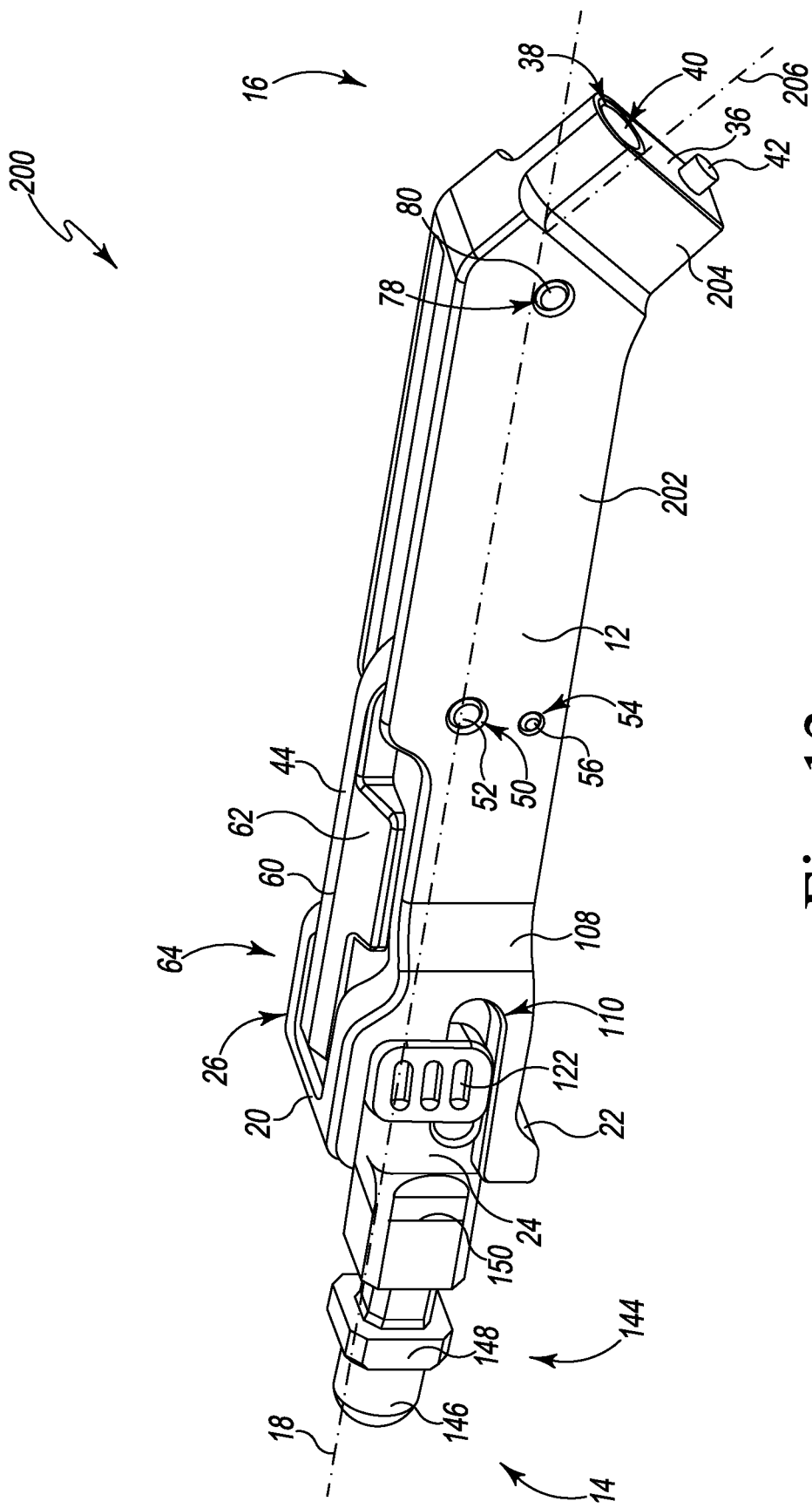
FIG. 13 is a perspective view of the curved broach impactor adapter of FIG. 11 in a latched configuration.
Figure 14:
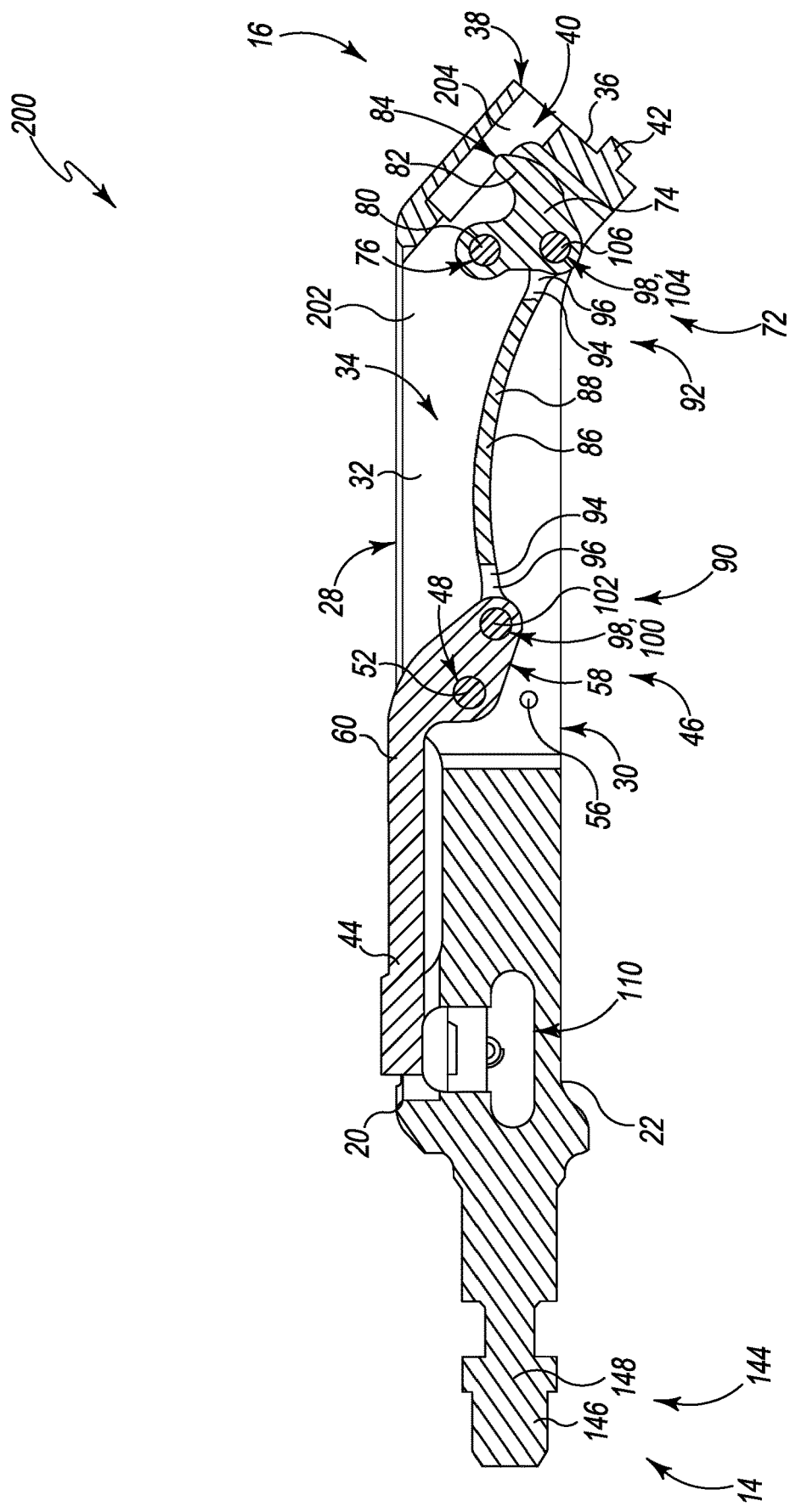
FIG. 14 is a cross-sectional elevation view of the curved broach impactor adapter of FIG. 13.
Figure 15:
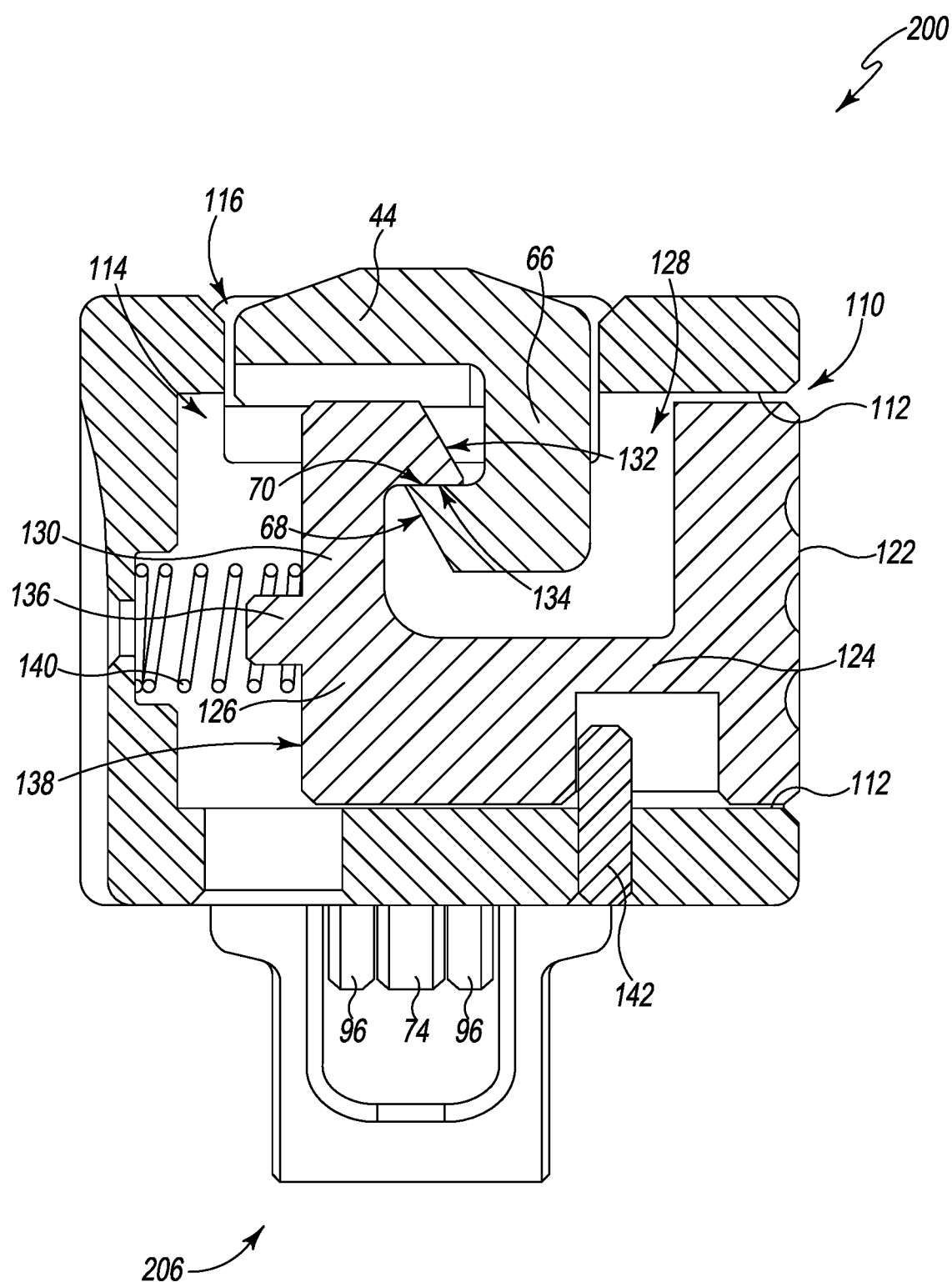
FIG. 15 is a cross-sectional rear elevation view of the curved broach adapter of FIG. 13.

After latching the impactor adapter 10, the surgeon attaches the impactor end 14 of the impactor adapter 10 to an automated surgical impactor 178 as shown in FIG. 10. Additionally or alternatively, in some embodiments the impactor adapter 10 may be attached to the automated surgical impactor 178 before being attached to the femoral broach 152.

The automated surgical impactor 178 may be embodied as a Kincise™ surgical automated system component commercially available from DePuy Synthes of Warsaw, Indiana. In the illustrative embodiment, the automated surgical impactor 178 includes an impactor body 180 having a twist-lock collar 182 and a battery pack 184. Electrical drive components 186 are housed within the impactor body 180. The impactor body 180 further includes a primary hand grip 188, a secondary hand grip 190, and a trigger 192.

In use, the surgeon inserts the shank 144 of the impactor adapter 10 into the twist-lock collar 182 and then locks the collar 182 on to the shank 144. Holding the primary hand grip 188 and/or the secondary hand grip 190, the surgeon inserts the femoral broach 152 into the surgically prepared femur 194 of the patient as shown in FIG. 10. After positioning the femoral broach 152, the surgeon depresses the trigger 192, which causes the electrical drive components 186 to generate a series of controlled percussive impacts on the impactor adapter 10 using electrical energy provided by the battery pack 184. The impactor adaptor 10 communicates impaction force from the percussive impacts to the femoral broach 152, thereby driving the femoral broach 152 into the medullary canal of the patient's femur 194. During impaction, the surgeon's hands may remain on the automated surgical impactor 178, and the latch lever 44 remains in the latched position. Additionally, the leaf spring 86 retains the femoral broach 152 rigidly against the impactor adaptor 10 during impaction. Unlike adapters using a typical rigid drive train attachment mechanism, the compliant, flexible leaf spring 86 of the impactor adapter 10 may not back out or otherwise loosen during impaction, even when subject to frequent, lower-amplitude impactions generated by the automated surgical impactor 178.

After the femoral broach 152 has been broached to a desired depth or otherwise fully impacted into the patient's femur 194, the surgeon may remove the femoral broach 152 from the femur 194. For example, the surgeon may remove the femoral broach 152 in order to continue broaching the femur 194 with successively larger broaches 152. Additionally or alternatively, the surgeon may remove the femoral broach 152 in order to insert a prosthetic component, a trial component, or other femoral component into the femur 194. To remove the femoral broach 152, the surgeon operates the trigger 192 in a reverse mode, which generates a series of controlled percussive impacts on the impactor adapter 10 in a reverse direction, which backs the broach 152 out of the femur 194.

After removing the broach 152 from the femur 194, the surgeon removes the impactor adaptor 10 from the femoral broach 152. To do so, the surgeon depresses the button surface 122 of the pushbutton catch 120, causing the pushbutton catch 120 to slide into the cavity 114 in the body 12. As the pushbutton catch 120 slides into the cavity 114, the lower surface 134 disengages the upper surface 70 of the latch 66, which releases the latch end 64 of the latch lever 44. With the latch 66 released, the leaf spring 86 may urge the latch lever 44 to swing toward the open position. The surgeon may manually open the latch lever 44 as necessary, for example using the wing 62 as a grip surface. As described above, in the fully open position, the latch lever 44 is limited to an angle of about 40 degrees. This limited open angle may have a low risk of snagging, tearing, or otherwise interfering with the patient's tissue. After moving the latch lever 44 to the open position, the clamp lever 72 is released from the mounting post 168, and the broach 152 may be removed from the impactor adaptor 10. After removing the broach 152, another femoral broach 152, for example of a larger size, may be attached to the impactor adapter 10 as described above.

Although the femoral broach 152 is described as being removed from the femur 194 prior to being removed from the impactor adapter 10, it should be understood that in some embodiments the impactor adapter 10 may be removed from the broach 152 while the broach 152 remains positioned in the femur 194. For example, in certain embodiments the final, largest broach 152 used by the surgeon may remain in the femur 194 for use as a femoral trial component.

As described above, the elongated body 12 of the impactor adapter 10 has a generally linear shape that defines a longitudinal tool axis 18. This linear shape of the impactor adapter 10 may be selected by surgeons who employ a direct anterior approach (DAA) surgical technique for performing hip replacements. Impactor adaptors with other shapes may be used for other surgical approaches.

Referring now to FIGS. 11-15, an illustrative embodiment of a curved broach impactor adapter 200 may be used in a posterior approach surgical technique and/or an anterolateral approach surgical technique for performing hip replacements. The illustrative curved impactor adaptor 200 shares similar components to the straight broach adapter 10. Those similar components are shown in FIGS. 11-15 with the same reference numbers shown in FIGS. 1-5, and the description of those components is not repeated here so as not to obscure the present disclosure.

Different from the impactor adaptor 10 shown in FIGS. 1-5, the curved adapter 200 shown in FIGS. 11-15 includes an elongated body 12 having a straight segment 202 and a curved segment 204. The straight segment 202 extends in line with the tool axis 18. The curved segment 204 defines a broach axis 206 extending outward from the broach end 16. A nonzero angle is defined between the tool axis 18 and the broach axis 206. As an additional difference with the impactor adapter 10, the shank 144 of the curved adapter 202 extends in line with the tool axis 18.

Figure 16:
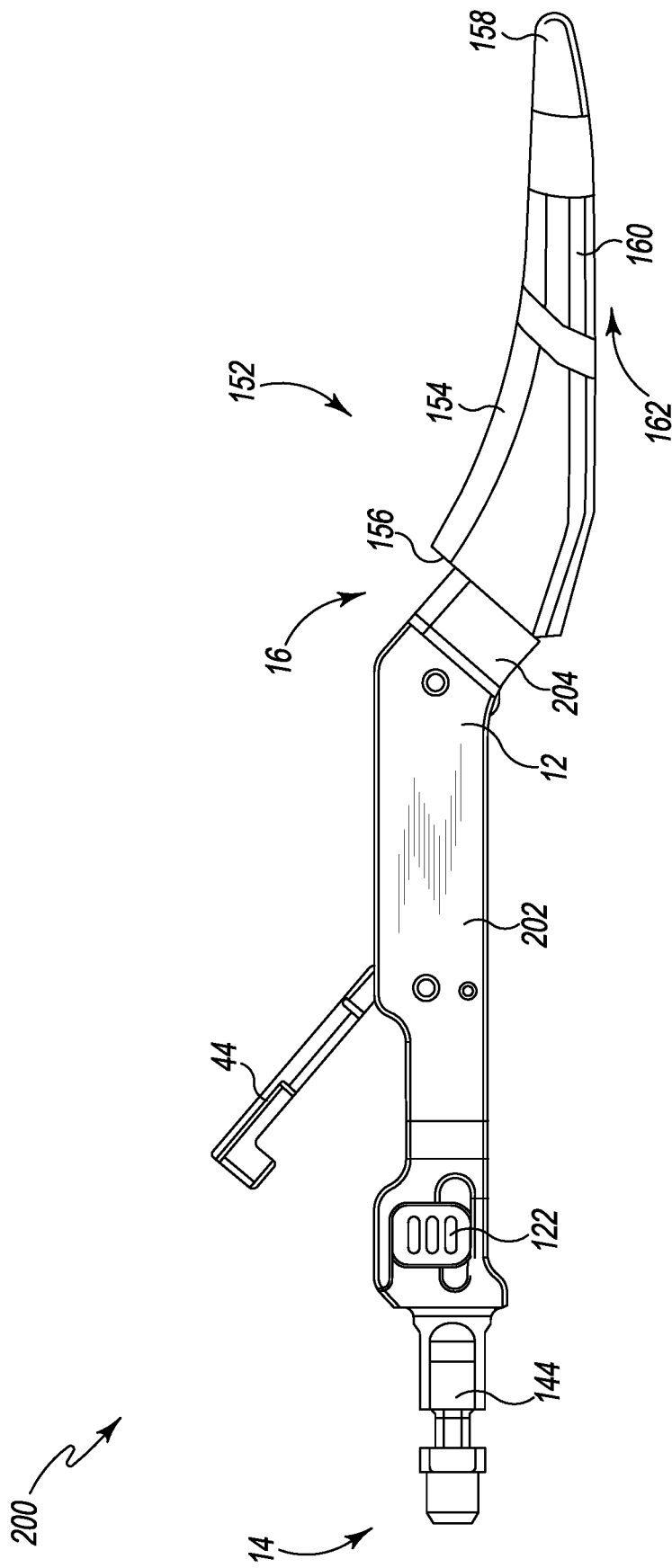
FIG. 16 is an elevation view of the curved broach impactor adapter of FIGS. 11-15 coupled to a femoral broach and in the open configuration.
Figure 17:
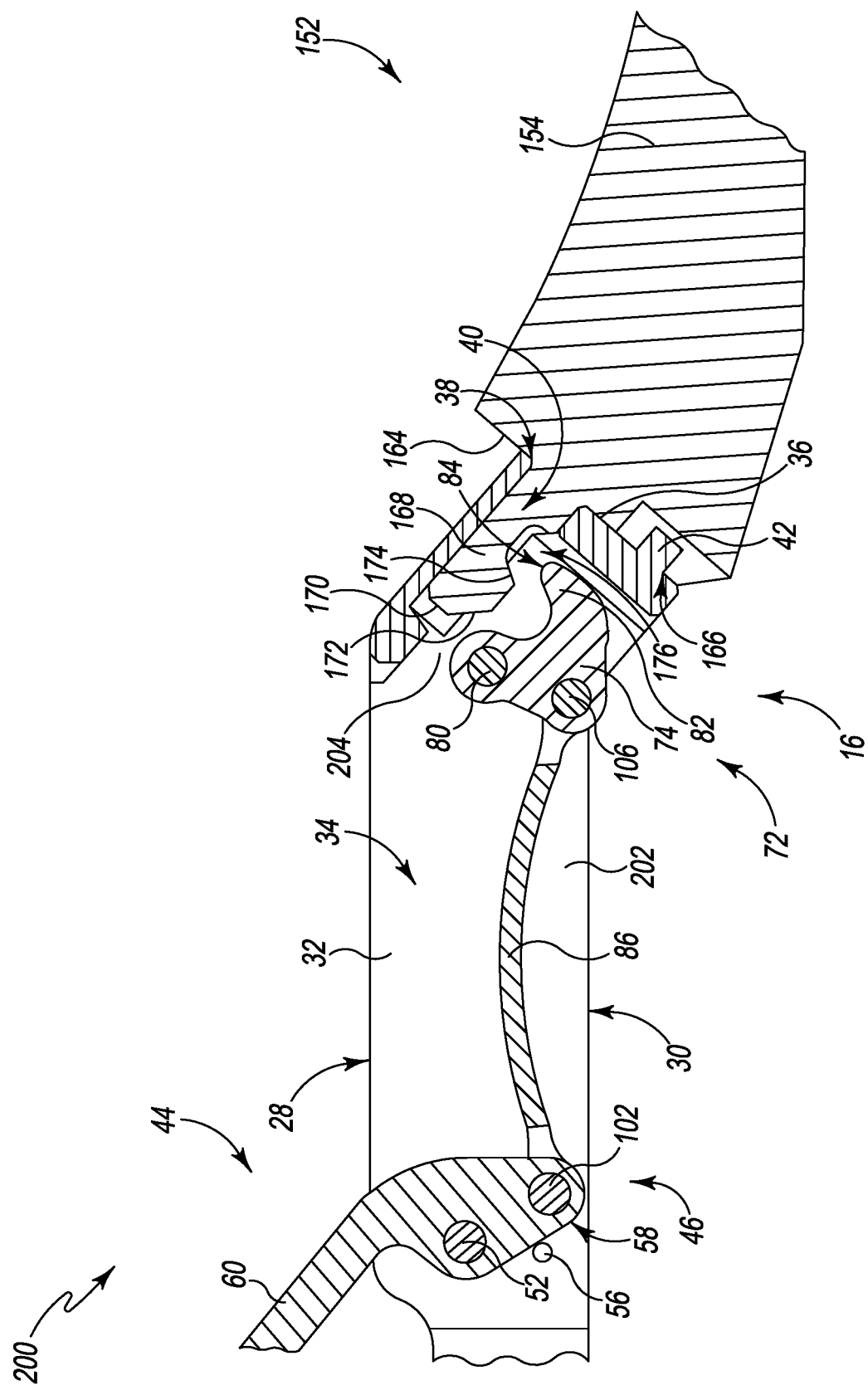
FIG. 17 is a fragmentary cross-sectional elevation view of the curved broach impactor adapter and the femoral broach of FIG. 16.
Figure 18:
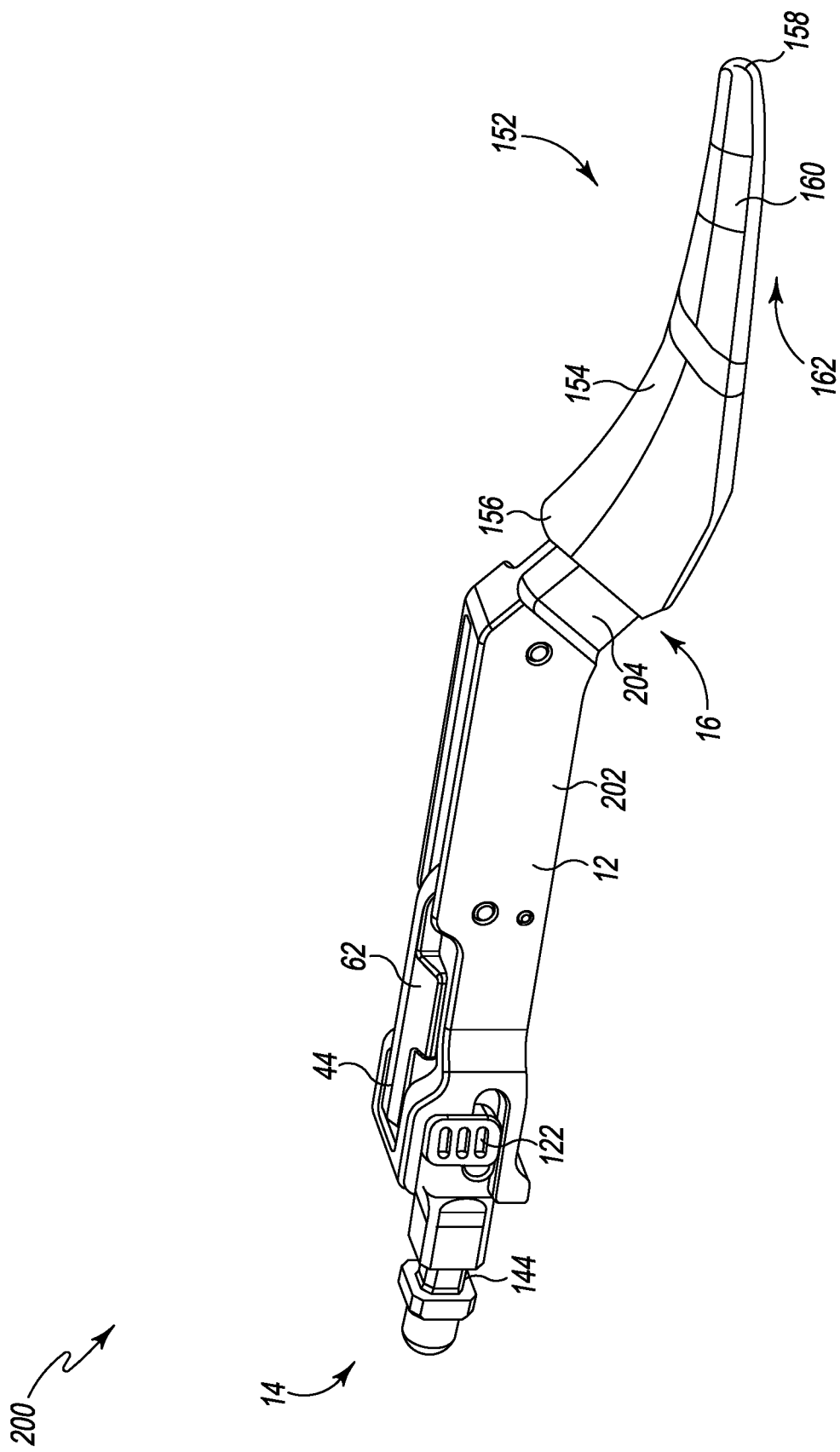
FIG. 18 is an elevation view of the curved broach impactor adapter of FIGS. 11-15 attached to the femoral broach and in the latched configuration.
Figure 19:
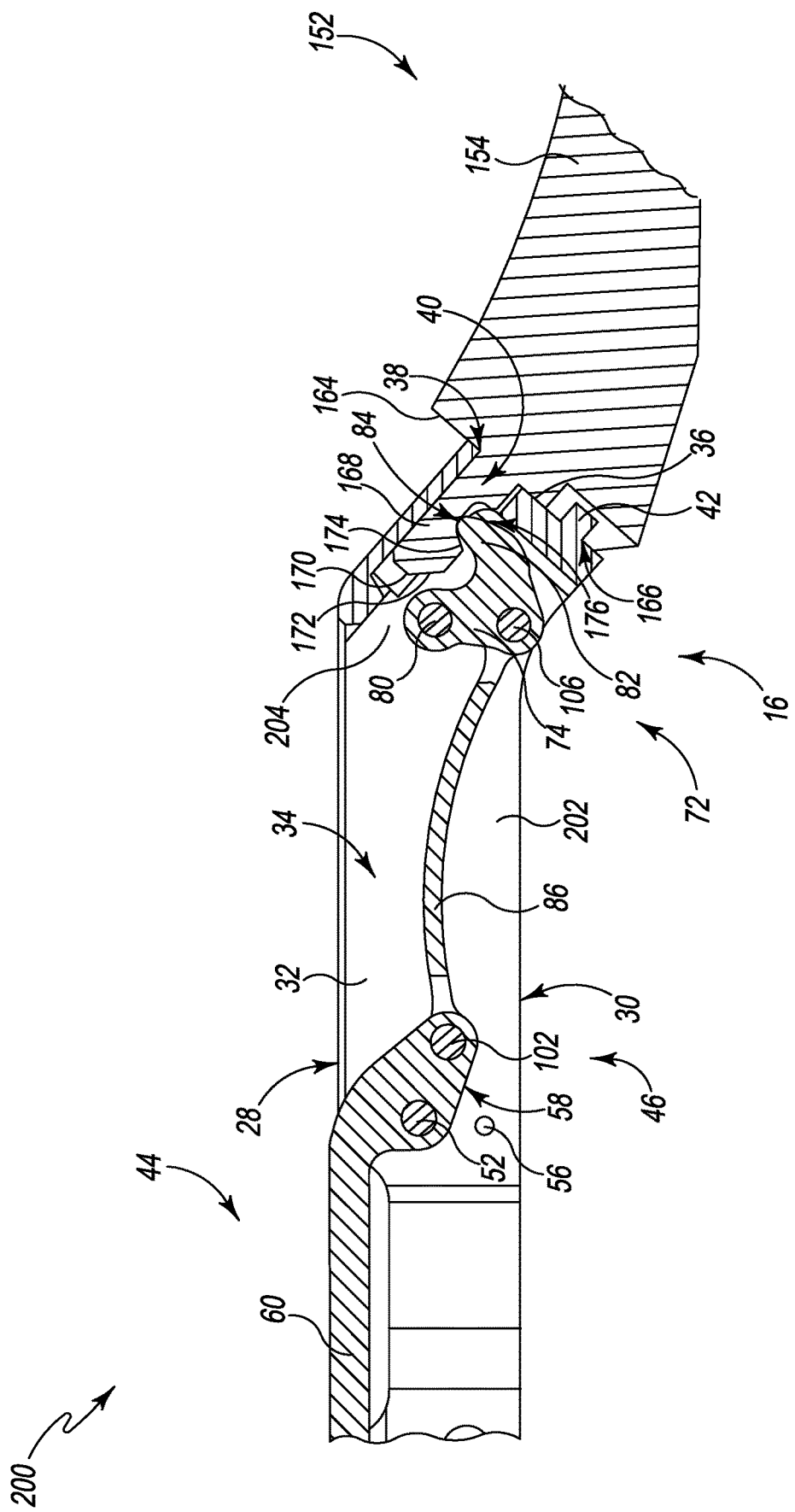
FIG. 19 is a fragmentary cross-sectional elevation view of the curved broach impactor and the femoral broach of FIG. 18.
Figure 20:
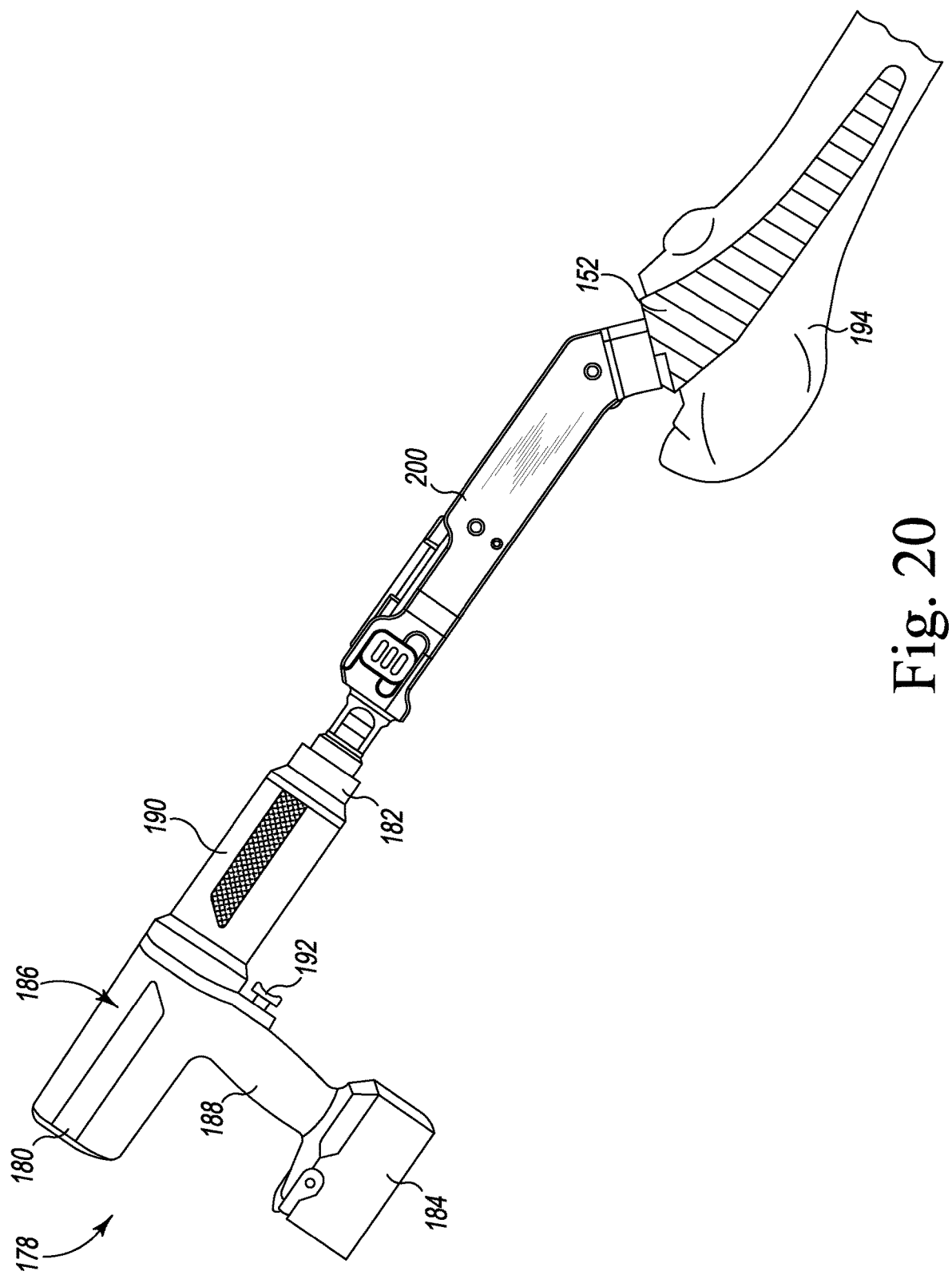
FIG. 20 is a perspective view of the curved broach impactor adapter and the femoral broach of FIGS. 18-19 during the performance of an orthopaedic surgical procedure using an automated surgical impactor.

The curved adapter 200 may be utilized during the performance of an orthopaedic surgical procedure as shown in FIGS. 16-20. The procedure shown in FIGS. 16-20 is similar to the procedure shown in FIGS. 6-10 and described above. As described above, initially a surgeon prepares the patient's bone to receive a surgical broach. As shown in FIGS. 16-17, the surgeon or other user attaches the femoral broach 152 to the broach end 16 of the curved adapter 200. As shown in FIGS. 18-19, once the femoral broach 152 is attached, the surgeon or other user moves the latch lever 44 from the open position to the latched position, in which the femoral broach 152 is held rigidly against the surface 36 of the curved adapter 200. As shown in FIG. 20, the surgeon attaches the impactor end 14 of the curved adapter 200 to the automated surgical impactor 178 and then impacts the broach 152 into the patient's femur 194 using the automated surgical impactor 178. As described above, the surgeon may impact the broach 152 using a posterior approach or an anterolateral approach. After completing broaching, the surgeon may remove the broach 152 from the curved adapter 200, for example to continue broaching with successively larger broaches 152, or to implant a femoral component or other prosthetic component.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument for use with a surgical broach, the orthopaedic surgical instrument comprising:
   an elongated body extending from a first end to a second end, wherein the first end is configured to be received by an automated surgical impactor;
   a first lever that extends from a pivot end to a latch end, wherein the pivot end is pivotally coupled to the elongated body;
   a second lever pivotally coupled to the elongated body, the second lever comprising a hook extending toward a top surface of the elongated body;
   a leaf spring having a first end that is pivotally coupled to the first lever and a second end that is pivotally coupled to the second lever such that movement of the first lever causes movement of the second lever, wherein the leaf spring comprises a flexible body extending between the first end of the leaf spring and the second end of the leaf spring;
   a stop pin coupled to the elongated body; and
   a pushbutton catch coupled to the elongated body, wherein the pushbutton catch comprises a button surface positioned toward a first side wall of the elongated body;

wherein the first lever is pivotally coupled to the elongated body at a first pivot point defined on the first lever and the leaf spring is pivotally coupled to the first lever at a second pivot point defined on the first lever, wherein the second pivot point is positioned between the first pivot point and the pivot end of the first lever;

wherein the first lever is movable between a first position in which the latch end is spaced apart from the elongated body and a second position in which the latch end is captured by the pushbutton catch, wherein when the first lever is in the second position the leaf spring is in compression urges the second lever to pivot the hook toward the top surface, and wherein when the first lever is in the second position a force exerted by the leaf spring urges the first lever to pivot about the first pivot point, wherein the latch end of the first lever is urged against the pushbutton catch toward the first position;

wherein when the first lever is in the first position a bottom surface of the pivot end of the first lever contacts the stop pin; and wherein the pushbutton catch is moveable between a first position in which the pushbutton catch engages the latch end of the first lever and a second position in which the pushbutton catch does not engage the latch end, wherein when the pushbutton catch moves from the first position to the second position the button surface moves within the elongated body in a direction transverse to a longitudinal tool axis defined by the elongated body.

2. The orthopaedic surgical instrument of claim 1, wherein the elongated body comprises a curved segment between the pivot end of the first lever and the second end of the elongated body.

3. The orthopaedic surgical instrument of claim 1, wherein:
the elongated body comprises: (i) the top surface having an elongated opening defined therein, (ii) a bottom surface opposite the top surface and having an elongated opening defined therein, (iii) one or more inner walls extending between the elongated opening defined in the top surface and the elongated opening defined in the bottom surface, and (iv) a first cavity defined by the one or more inner walls;
wherein the second lever is positioned within the first cavity;
wherein the pivot end of the first lever is pivotally coupled to the elongated body within the first cavity and wherein the latch end of the elongated lever extends out of the first cavity through the elongated opening defined in the top surface; and
wherein the leaf spring is positioned within the first cavity.

4. The orthopaedic surgical instrument of claim 3, wherein:
the elongated body comprises a planar front surface positioned on the second end of the elongated body; and
a circular aperture is defined in the planar front surface, wherein the circular aperture opens into the first cavity.

5. The orthopaedic surgical instrument of claim 4, wherein:
the circular aperture defines a passageway into the internal cavity that is sized to receive a mounting post of the surgical broach; and
when the first lever is in the second position the hook of the second lever is positioned in the passageway.

6. The orthopaedic surgical instrument of claim 5, wherein a guide post extends outward from the planar front surface of the elongated body, wherein the guide post is positioned between the circular aperture and the bottom surface.

7. The orthopaedic surgical instrument of claim 3, wherein the stop pin is positioned within the first cavity.

8. The orthopaedic surgical instrument of claim 3, wherein:
the elongated body comprises: (i) a second side wall opposite the first side wall, (ii) an opening defined in the first side wall, (iii) one or more inner walls extending inwardly from the opening in the first side wall, wherein the one or more inner walls define a second cavity, and (iv) a second opening defined in the top surface between the first end and the elongated opening, wherein the second opening opens into the second cavity;
the pushbutton catch is positioned in the second cavity; and
when the first lever is in the second position, a latch extending downward from the latch ending is positioned in the second cavity and retained by the pushbutton catch.

9. The orthopaedic surgical instrument of claim 8, wherein when the pushbutton catch is in the first position the pushbutton catch engages the latch positioned within the second cavity and when the pushbutton catch is in the second position the pushbutton catch does not engage the latch.

10. The orthopaedic surgical instrument of claim 9, further comprising a second spring positioned in the second cavity, wherein the second spring is configured to bias the pushbutton catch in the first position.

11. The orthopaedic surgical instrument of claim 10, wherein the pushbutton catch comprises a pair of side walls extending from the button surface into the second cavity, a back wall that connects the pair of side walls, and a catch that extends from the back wall into the second cavity.

12. The orthopaedic surgical instrument of claim 11, wherein the latch of the elongated lever comprises a first cam surface, wherein the catch of the pushbutton catch comprises a second cam surface, wherein when the first lever is moved from the first position to the second position, the first cam surface engages the second cam surface, and wherein when the first cam surface engages the second cam surface the pushbutton catch is urged from the first position to the second position.

13. An orthopaedic surgical instrument for use with a surgical broach, the orthopaedic surgical instrument comprising:
an elongated body extending from a first end to a second end and comprising a first side wall, wherein the elongated body defines a longitudinal tool axis, and wherein the first end is configured to be received by an automated surgical impactor;
a first lever that extends from a pivot end to a latch end, wherein the pivot end is pivotally coupled to the elongated body;
a second lever pivotally coupled to the elongated body, the second lever comprising a hook extending toward a top surface of the elongated body;
a leaf spring having a first end that is pivotally coupled to the first lever and a second end that is pivotally coupled to the second lever; and a pushbutton catch coupled to the elongated body, wherein the pushbutton catch comprises a button surface positioned toward the first side wall of the elongated body;

wherein the pushbutton catch is moveable between a first position and a second position, wherein in the first position the pushbutton catch engages the latch end of the first lever when the first lever is in a latched position, and wherein in the second position the pushbutton catch does not engage the latch end; and wherein when the pushbutton catch moves from the first position to the second position the button surface moves within the elongated body in a direction transverse to the longitudinal tool axis.

14. The orthopaedic surgical instrument of claim 13, wherein when the pushbutton catch is in the first position, the button surface of the pushbutton catch is positioned flush with the first side wall of the elongated body or is recessed within the elongated body from the first side wall.

15. The orthopaedic surgical instrument of claim 13, wherein the button surface of the pushbutton catch comprises a textured grip feature.

16. The orthopaedic surgical instrument of claim 13, further comprising a second spring positioned within the elongated body, wherein the second spring is configured to bias the pushbutton catch in the first position.

17. The orthopaedic surgical instrument of claim 13, wherein the pushbutton catch comprises a catch that extends within the elongated body, and wherein when the first lever is in the latched position, the latch of first lever is captured within the elongated body by the catch of the pushbutton catch.

18. The orthopaedic surgical instrument of claim 17, wherein the latch of the first lever comprises a first cam surface, wherein the catch of the pushbutton catch comprises a second cam surface, wherein when the first lever is moved from an open position in which the latch end is spaced apart from the elongated body to the latched position, the first cam surface engages the second cam surface, and wherein when the first cam surface engages the second cam surface the pushbutton catch is urged from the first position to the second position.

* * * * *